United States Patent
Equels et al.

(10) Patent No.: US 12,102,649 B2
(45) Date of Patent: Oct. 1, 2024

(54) METHODS AND COMPOSITIONS FOR TREATING ENDOMETRIOSIS

(71) Applicant: AIM ImmunoTech Inc., Ocala, FL (US)

(72) Inventors: Thomas K. Equels, Ocala, FL (US); David R. Strayer, Bryn Mawr, PA (US)

(73) Assignee: AIM ImmunoTech Inc., Ocala, FL (US)

( * ) Notice: Subject to any disclaimer, the term of this patent is extended or adjusted under 35 U.S.C. 154(b) by 0 days.

(21) Appl. No.: 17/769,986

(22) PCT Filed: Oct. 22, 2020

(86) PCT No.: PCT/US2020/056882
§ 371 (c)(1),
(2) Date: Apr. 18, 2022

(87) PCT Pub. No.: WO2021/081218
PCT Pub. Date: Apr. 29, 2021

(65) Prior Publication Data
US 2022/0387475 A1    Dec. 8, 2022

Related U.S. Application Data

(60) Provisional application No. 63/065,475, filed on Aug. 13, 2020, provisional application No. 63/065,476, filed on Aug. 13, 2020, provisional application No. 62/931,098, filed on Nov. 5, 2019, provisional application No. 62/924,591, filed on Oct. 22, 2019.

(51) Int. Cl.
| | |
|---|---|
| *A61K 31/7105* | (2006.01) |
| *A61K 9/00* | (2006.01) |
| *A61K 31/713* | (2006.01) |
| *A61K 35/17* | (2015.01) |
| *A61P 15/00* | (2006.01) |

(52) U.S. Cl.
CPC ........ *A61K 31/7105* (2013.01); *A61K 9/0024* (2013.01); *A61K 35/17* (2013.01); *A61P 15/00* (2018.01); *A61K 31/713* (2013.01)

(58) Field of Classification Search
CPC ........... A61P 35/00; A61K 35/17; A61K 9/00; A61K 23/00
See application file for complete search history.

(56) References Cited

U.S. PATENT DOCUMENTS

| | | | | |
|---|---|---|---|---|
| 8,247,174 | B2 * | 8/2012 | Giudice | C12Q 1/68 435/6.1 |
| 2010/0266680 | A1 * | 10/2010 | Andre | A61P 31/00 424/139.1 |
| 2011/0150894 | A1 | 6/2011 | Ingber et al. | |
| 2014/0335112 | A1 * | 11/2014 | Carter | A61P 31/12 424/278.1 |
| 2015/0132295 | A1 * | 5/2015 | Hatchwell | C12Q 1/6883 514/12.7 |

FOREIGN PATENT DOCUMENTS

| | | |
|---|---|---|
| WO | 03/070910 A2 | 8/2003 |
| WO | 2005/045032 A2 | 5/2005 |
| WO | 2010/113507 A1 | 10/2010 |

OTHER PUBLICATIONS

Jan Lipfert at al. (Double-Stranded RNA under force and torque: Similarities to and striking differences from double-stranded DNA, PNAS, 111(43), 15408-15413. (Year: 2014).*
Svenja Allhorn et al. TLR3 and TLR4 expression in healthy and diseased human endometrium, Reproductive Biology and Endocrinology, 6;40. (Year: 2008).*
Carrnen Maria Carcia-Pascual et al., Evaluation of the potential therapeutic effects of a double-stranded RNA mimic complexed with polycations in an experimental mouse model of endometriosis, Fertility and sterility vol. 104(5), 1310-1318. (Year: 2015).*
International Search Report issued in PCT/US2020/056882; mailed Mar. 8, 2021.
Carmen Maria García-Pascual et al. "Evaluation of the Potential Therapeutic Effects of a Double-Stranded RNA Mimic Complexed With Polycations in an Experimental Mouse Model of Endometriosis" Fertility and Sterility, Nov. 2015, pp. 1310-1318, vol. 104 No. 5.
International Preliminary Report on Patentability and Written Opinion issued in PCT/US2020/056882; issued Apr. 26, 2022.
An Office Action issued by the Canadian Patent Office on Jul. 26, 2023, which corresponds to Canadian Patent Application No. 3,155,360 and is related to U.S. Appl. No. 17/769,986.
García-Pascual, "Evaluation of the potential therapeutic effects of a double-stranded RNA mimic complexed with polycations in an experimental mouse model of endometriosis", Fertil Steril, 104(5), pp. 1310-1318, Aug. 18, 2015 (Aug. 18, 2015) [Previously Cited on Apr. 18, 2022.].
Mitchell, W.M., "Efficacy of rintatolimod in the treatment of chronic fatigue syndrome/myalgic encephalomyelitis (CFS/ME)", Review Expert Rev Clin Pharmacol, 9(6), pp. 755-770, Jun. 2016 (Jun. 2016).
Extended Supplementary Search Report issued by the European Patent Office on Feb. 6, 2024, which corresponds to U.S. Appl. No. 17/769,986 and is related to U.S. Appl. No. 17/769,986.
Egorova et al. "Anti-angiogenic treatment of endometriosis via anti-VEGFA siRNA delivery by means of peptide- based carrier in a rat subcutaneous model", Gene Therapy, 25(8), pp. 548-555, Sep. 25, 2018 (Sep. 25, 2018).
Navabi et al. "A clinical grade poly I:C-analogue (AmpligenA (R)) promotes optimal DC maturation and Th1-type T cell responses of healthy donors and cancer patients in vitro", Vaccine, 27(1), pp. 107-115, Jan. 1, 2009 (Jan. 1, 2009).
Jasani et al. "Ampligen: A potential Toll-like 3 receptor adjuvant for immunotherapy of cancer", Vaccine, 27(25-26), pp. 3401-3404, May 26, 2009 (May 26, 2009).

(Continued)

*Primary Examiner* — Michael G. Hartley
*Assistant Examiner* — Jagadishwar R Samala
(74) *Attorney, Agent, or Firm* — Studebaker & Brackett PC

(57) ABSTRACT

Disclosed is a method for treating endometriosis, preventing endometriosis, or ameliorating a symptom of endometriosis in a subject comprising the step of administering to the subject a therapeutically effective amount of a pharmaceutical composition comprising as an active ingredient a therapeutic dsRNA (tdsRNA).

19 Claims, 8 Drawing Sheets

(56) References Cited

OTHER PUBLICATIONS

Frysh "How Endometriosis and Endometrial Cancer Differ" WebMD, May 14, 2022; www.webmd.com/women/endometriosis/endometriosis-endometrial-cancer-difference; three pages.

Galzerano "Endometriosis vs. Endometrial Cancer: Key Differences You Should Know" Jefferson Health; Mar. 17, 2022; www.jeffersonhealth.org/your-health/living-well/endometriosis-vs-endometrial-cancer-key-differences-you-should-know; four pages.

\* cited by examiner

METHODS AND COMPOSITIONS FOR TREATING ENDOMETRIOSIS

CROSS-REFERENCE TO RELATED APPLICATIONS

This application is the U.S. National Stage of International Application No. PCT/US2020/056882 filed Oct. 22, 2020, which claims benefit of priority to U.S. Provisional Application No. 62/924,591 filed Oct. 22, 2019; U.S. Provisional Application No. 62/931,098 filed Nov. 5, 2019; U.S. Provisional Application No. 63/065,475 filed Aug. 13, 2020; and U.S. Provisional Application No. 63/065,476 filed Aug. 13, 2020, the entire content of which is incorporated herein by reference.

BACKGROUND

Endometriosis is an inflammatory disease affecting women of reproductive age. The hallmark of endometriosis is the presence of endometrium-like tissue in the pelvic peritoneum and ovaries. Growth of ectopic tissue in endometriosis patients leads to chronic pelvic pain, painful menstrual cramps, long-term pain in the lower back and pelvis, pain during intercourse, and infertility. Globally there are over 176 million women with endometriosis and this disorder is a common chronic debilitating disease in the United States that affects 5 percent (3.2 million) to 10 percent (6.4 million) of women of reproductive age.

BRIEF DESCRIPTION

One embodiment is directed to a method for treating endometriosis, preventing endometriosis, preventing a reoccurrence of endometriosis, or ameliorating (i.e., reducing) a symptom of endometriosis in a subject comprising the step of administering to the subject a therapeutically effective amount of a pharmaceutical composition comprising as an active ingredient a therapeutic dsRNA (tdsRNA). The endometriosis being treated may be, for example, reoccurring endometriosis.

The symptoms of endometriosis may be, at least, one selected from the group consisting of dyspareunia; dysmenorrhea; chronic pelvic pain; dyspareunia; dysuria; mittelschmerz; interstitial cystitis; pelvic inflammatory disease; and bodily movement pain present during exercise, standing and walking.

Administering (or administration) may be any form known such as, for example, at least one form of administering selected from the group consisting of: administering intravenously; administering intraperitoneally; administering intranasally; administering intradermally; administering subcutaneously; administering intramuscularly; administering intracranially; administering intravesically; administering orally; and administering topically.

It is preferred that the subject be any female mammal that menstruates. It is preferred that the subject is a human female. It is most preferred that the subject is a human female between menarche and menopause.

In one embodiment, administering may be administering to a subject intraperitoneally one to three times a week and wherein the dosage would be 50-400 mg tdsRNA per day (or effectively or on average per day), for up to one month or longer than one month. For example, administration of 100 mg every other day would result in an administration of 50 mg per day.

In another embodiment, the pharmaceutical composition is administered to the subject intravenously twice a week at 400 mg tdsRNA per dose.

In another embodiment, the pharmaceutical composition is administered to the subject orally one to three times a week at a dosage of 100 to 400 mg of active ingredient per day continuously for at least one month.

The tdsRNA in any composition or method of this disclosure may be at least one selected from the group consisting of $$rI_n \cdot r(C_xU)_n \quad \text{(formula 1);}$$

$$rI_n \cdot r(C_xG)_n \quad \text{(formula 2);}$$

$$rA_n \cdot rU_n \quad \text{(formula 3);}$$

$$rI_n \cdot rC_n \quad \text{(formula 4);}$$

$$\text{rugged dsRNA} \quad \text{(formula 5);}$$

wherein x is one or more selected from the group consisting of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 4-29, 11-14, and 30-35.

In any embodiment, the tdsRNA may contain a minimum of 90 weight percent of dsRNA which is larger than a size selected from the group consisting of: 40 basepairs; 50 basepairs; 60 basepairs; 70 basepairs; and 80 basepairs.

In any embodiment, the tdsRNA may contain a minimum of 90 weight percent of dsRNA which is smaller than a size selected from the group consisting of: 10,000 basepairs; 9000 basepairs; 8000 basepairs; and 7000 basepairs.

In any embodiment, the rugged dsRNA may have a strand comprised of $r(C_{4-29}U)$, $r(C_{11-14}U)$, or $r(C_{12}U)$; and an opposite strand comprised of $r(I)$; wherein the two strands do not base pair the position of the uracil base, wherein said strands are partially hybridized; and wherein the rugged dsRNA has a molecular weight of about 250 kDa (kiloDaltons) to about 320 kDa.

In any embodiment, the rugged dsRNA may have a strand comprised of $r(C_{4-29}U)$, $r(C_{11-14}U)$, or $r(C_{12}U)$; and an opposite strand comprised of $r(I)$; wherein the two strands do not base pair the position of the uracil base, wherein said strands are partially hybridized; and wherein each strand is from about 380 bases to about 450 bases.

In any embodiment, the rugged dsRNA may have a strand comprised of $r(C_{4-29}U)$, $r(C_{11-14}U)$, or $r(C_{12}U)$; and an opposite strand comprised of $r(I)$; wherein the two strands do not base pair the position of the uracil base, wherein said strands are partially hybridized; and wherein the tdsRNA has about 30 to about 38 helical turns of duplexed RNA.

In any embodiment, the rugged dsRNA may have a strand comprised of $r(C_{4-29}U)$, $r(C_{11-14}U)n$, or $r(C_{12}U)n$; and an opposite strand comprised of $r(I)$; wherein the two strands do not base pair the position of the uracil base, and wherein said strands are partially hybridized. The rugged dsRNA may have at least one of the following characteristics selected from the group consisting of: the rugged dsRNA has a molecular weight of about 250 kDa to about 320 kDa or about 250 kDa to 500 kDa; each strand of the rugged dsRNA is from about 380-450 basepairss or about 400-800 basepairs in length; and the tdsRNA has about 30 to about 38 helical turns of duplexed RNA or about 30 to 100 helical turns of duplexed RNA.

In any embodiment, n may be from 40 to 500 or from 40 to 40,000.

In any embodiment, the tdsRNA may have about 4.0 to about 50 helical turns of duplexed RNA strands, or about 4.0 to about 4000 helical turns of duplexed RNA strands.

In any embodiment, the tdsRNA has a molecular weight from about 24 kilodalton to about 300 kilodalton or from about 24 kilodalton to about 2500 kilodalton.

In any embodiment, wherein the tdsRNA comprises a rugged dsRNA weight percent greater than a value selected from the group consisting of: 30 weight percent; 40 weight percent; 50 weight percent; 60 weight percent; 70 weight percent; 80 weight percent; and 90 weight percent.

In any embodiment, the tdsRNA may be a linear structure without a branching RNA structure.

In any embodiment, at least 25 weight percent, at least 50 weight percent, or at least 75 weight percent of the therapeutic dsRNA is a linear structure without a branching RNA structure.

In any embodiment, the pharmaceutical composition may comprise tdsRNA wherein at least 30 weight percent of total dsRNA is a linear structure; at least 40 weight percent of total dsRNA is a linear structure; at least 50 weight percent of total dsRNA is a linear structure; at least 60 weight percent of total dsRNA is a linear structure; at least 70 weight percent of total dsRNA is a linear structure; at least 80 weight percent of total dsRNA is a linear structure; or at least 90 weight percent of total dsRNA is a linear structure.

In any embodiment, the tdsRNA may comprise $rI_n \cdot ribo(C_{11-14}U)n$; and rugged dsRNA.

In any method, the method may further comprise a step of administering an interferon to the subject before, after, or at the same time as administering the tdsRNA. That is, the steps of administering the tdsRNA and administering the interferon are performed in any order (e.g., before, after, at the same time). The interferon may be at least one selected from the group consisting of: interferon, interferon mixture, Alferon, alpha-interferon species, recombinant or natural interferon alpha, recombinant or natural interferon alpha 2a, recombinant or natural interferon beta, recombinant or natural interferon beta 1b, recombinant, and natural interferon gamma. Any interferon of this disclosure can encompass a natural or recombinant interferon. A recombinant interferon may be an interferon produced (expressed) using recombinant nucleic acid technology.

The interferon may be interferon species purified as a mixture of at least seven species of alpha-interferon produced by human white blood cells. The seven species may be, for example, interferon alpha 2; interferon alpha 4; interferon alpha 7; interferon alpha 8; interferon alpha 10; interferon alpha 16; and interferon alpha 17.

In a preferred embodiment, the subject has an ectopic endometrial growth and the method produces at least one effect in the ectopic endometrial growth selected from the group consisting of: an increase in macrophage activity; an increase in NK cell activity; and an increase in T effector cell/T regulatory cell ratio.

In another preferred embodiment, the method produce at least one effect in the peritoneal cavity selected from the group consisting of: an increase in macrophage activity; an increase in NK cell activity; and an increase in T effector cell/T regulatory cell ratio.

Another embodiment is directed to a composition for treating endometriosis, preventing endometriosis, preventing a reoccurrence of endometriosis, or ameliorating a symptom of endometriosis in a subject comprising:

tdsRNA selected from the group consisting of $$rI_n \cdot r(C_xU)_n \quad \text{(formula 1)};$$

$$rI_n \cdot r(C_xG)_n \quad \text{(formula 2)};$$

$$rA_n \cdot rU_n \quad \text{(formula 3)};$$

$$rI_n \cdot rC_n \quad \text{(formula 4)};$$

$$\text{rugged dsRNA} \quad \text{(formula 5)};$$

wherein x is one or more selected from the group consisting of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 4-29, 11-14, and 30-35. In a preferred embodiment, the composition comprises $rI_n \cdot ribo(C_{11-14}U)_n$; and rugged dsRNA. In a more preferred embodiment, the composition comprises $rI_n \cdot ribo(C_{12}U)_n$; and rugged dsRNA. The composition can optionally comprise an interferon which can be a natural or a recombinant interferon. The interferon may be any interferon or combinations of interferon described in this disclosure. For example, the interferon may be selected from the group consisting of: natural or recombinant interferon, Alferon, alpha-interferon species, recombinant or natural interferon alpha, recombinant or natural interferon alpha 2a, recombinant or natural interferon beta, recombinant or natural interferon beta 1b, recombinant, and natural interferon gamma. As another example, the interferon may be interferon species purified as a mixture of at least seven species of alpha-interferon produced by human white blood cells. The seven species may be, for example, interferon alpha 2; interferon alpha 4; interferon alpha 7; interferon alpha 8; interferon alpha 10; interferon alpha 16; and interferon alpha 17.

DETAILED DESCRIPTION

Figure 1:
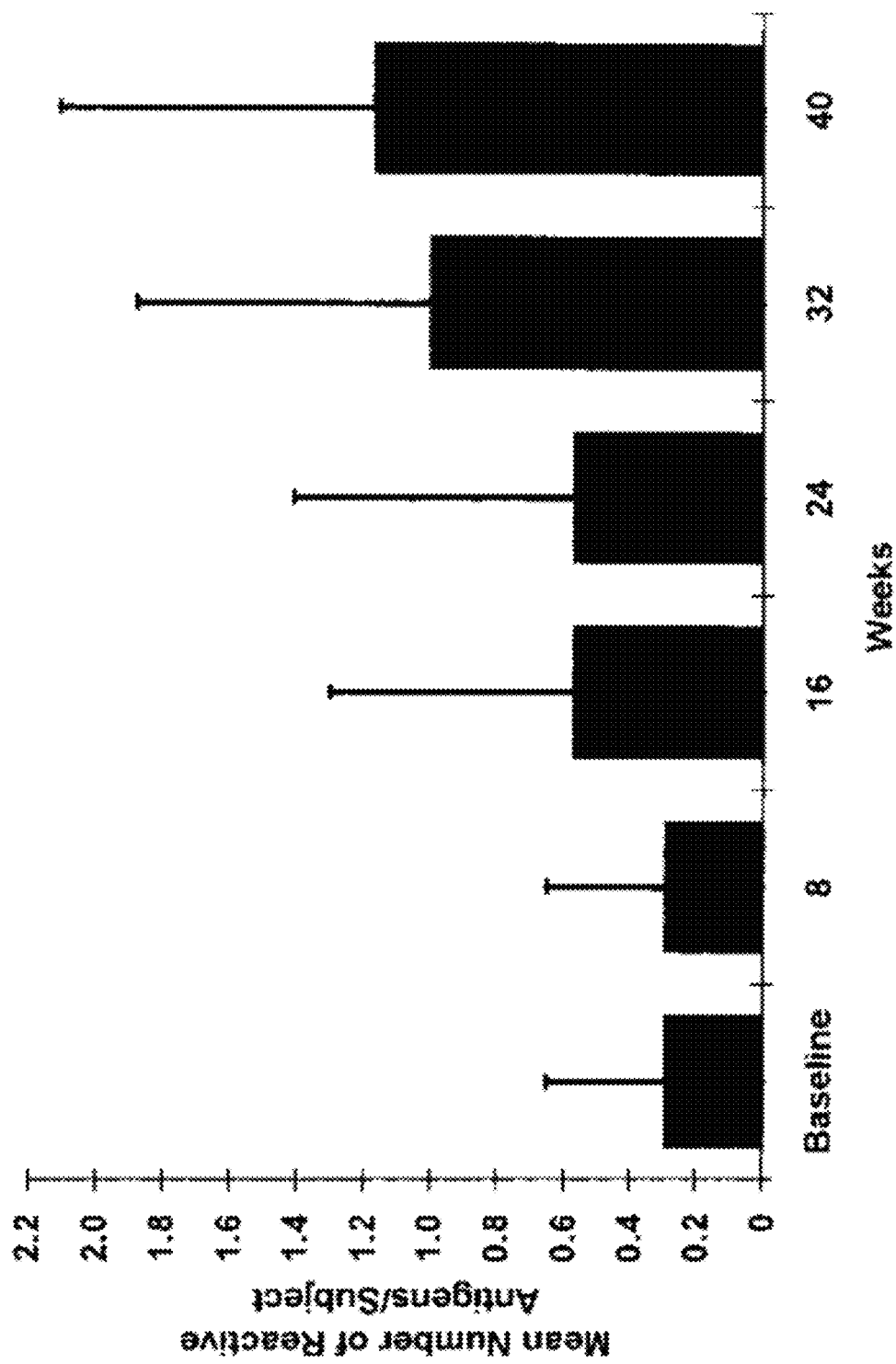
FIG. 1 shows that tdsRNA can augment delayed-type hypersensitivity in HIV patients with depressed cellular immunity and that the augmentation increases with repeated administration.

The present disclosure relates to methods and prophylactic and/or therapeutic agents for treating endometriosis and recurring endometriosis. Treatment may involve the prevention or reduction of endometriosis and/or associated symptoms thereof. The methods and prophylactic and/or therapeutic agents have, as an active ingredient, a therapeutic double-stranded RNA.

Current pharmaceutical and surgical methods are less than ideal for treating endometriosis. Most current pharmacological treatments are not suitable for long-term usage due to their side-effect profile. For example, while endometriosis is a chronic condition, the FDA approved drug for treating some symptoms of endometriosis, Orilissa®, has a maximum recommended treatment duration of only 6 months. Although endometriosis may be treated by surgical excision of the ectopic endometriotic tissue, this method is less than optimal because complete surgical excision is difficult to achieve. As a result, endometriosis commonly recurs after one surgery and multiple surgeries are often required for a complete treatment.

At this time, both medical and surgical approaches for endometriosis fails to deliver real relief to patients. For example, in the two Orilissa® randomized, placebo-controlled trials used to obtain FDA approval, the mean relief in pain from endometriosis without other co-existing conditions was only an 11.4% decrease. As discussed above, multiple surgical procedures are required for treatment and each surgical procedure would involve some pain.

One proposed mechanism of the development of endometriosis involves fragments of menstrual endometrium passing by retrograde flow through the fallopian tubes with implantation on peritoneal surfaces with growth and persistence which, eventually, leads to the symptoms of endometriosis. This mechanism has been observed in humans and is supported by primate models. The fact that endometriosis only occurs in species that menstruate also support this model. However, since retrograde menstruation likely occurs in the majority of women, additional mechanisms are required to explain why only 5 to 10 percent of women of reproductive age develop endometriosis.

Another likely contributing mechanism is that one or more defects in the immune system is a contributing mechanism to endometriosis. That is because for endometriosis to be established, the endometrial tissue must evade normal immune surveillances as it implants and grows on the peritoneal surfaces following retrograde menstruation. Studies on endometriosis patients tend to support this mechanism.

Characterization of the cellular component in the peritoneal fluid of women with endometriosis shows disturbances in cellular immunity can contribute to the progression of endometriosis in the peritoneal cavity consistent with the models discussed above. This immune defect leading to tolerance of the ectopic endometrial tissue includes a decrease in phagocytosis by macrophages and decreases in NK cell activity in the peritoneal cavity. Decrease in innate and cellular immunity is thought to be a manifestation of the decrease in immunosurveillance which allows the fragments of menstrual endometrium to implant and grow on the peritoneal surfaces. Surprisingly, in this disclosure, we have shown that these decreases in the subject can be reversed by administering tdsRNA to the subject. See, for example, Table 2 and Table 3 below and the experiments in the Examples below.

tdsRNA has activities which reverses some of the biological processes that render a person more susceptible to endometriosis. Endometriosis patients suffer from 3 symptoms as follows: (1) decrease in macrophage activity; (2) decrease in NK cell activity; and (3) decrease in T effector cell/T regulatory cell ratio. This disclosure shows that tdsRNA, when administered to a subject, has the ability to change the microenvironment in endometriosis tissue to reverse the above-listed symptoms to cause regression of ectopic endometriosis tissue. By causing the regression of ectopic endometriosis tissue, the disease is treated or, at least, one or more symptoms of the disease is reduced.

Briefly, in this disclosure, we have shown that tdsRNA (including AMPLIGEN®) enhances NK Cell Activity and Macrophage Activity in Mice (See, Example 3 and Table 2) and in humans (See, Example 4, Table 3 and FIG. 1); and tdsRNA (including AMPLIGEN®) has a beneficial effect on enhancing immunosurveillance to reduce ectopic growth from a variety of models. Specifically, the disclosure shows tdsRNA increases the ratio of effector T cells to regulatory T cells ($T_{effector}/T_{reg}$) in the ectopic environment with colorectal carcinoma as the ectopic tissue model (See, Example 6, and FIG. 2, FIG. 3 and FIG. 4). Consistent with our model, mouse data also show that tdsRNA has a beneficial effect on suppressing ectopic growth and increased survival in mice with ectopic pancreatic growth model (see, Example 9, Table 4), with melanoma tumors as an ectopic tissue growth model (See, Example 10, Table 5, Example 7, Tables 6, 7, 8, 9), with colorectal cancer as an ectopic tissue growth model (Example 8, FIG. 5), with bladder carcinoma as an ectopic tissue growth model (Example 6), and with renal carcinoma as an ectopic tissue growth model (See, Example 8, FIG. 5, FIG. 6). Further, tdsRNA is shown to be effective in treating endometriosis in two human trials (see, Examples 12 and 13) for at least the symptoms in the following table.

TABLE 1

Major Symptoms of Ectopic Tumor Tissue Growth in the Peritoneal Cavity of Patients with Endometriosis dyspareunia
dysmenorrhea
chronic pelvic pain
dyspareunia
dysuria
mittelschmerz
interstitial cystitis
pelvic inflammatory disease
bodily movement pain present during exercise, standing and walking

1. General Definitions

This disclosure relates to, inter alia, tdsRNA. tdsRNA can also be called "therapeutic dsRNA," or "therapeutic double stranded RNA" and these terms have the same meaning.

"r" and "ribo" has the same meaning and refer to ribonucleic acid or the nucleotide or nucleoside that are the building block of ribonucleic acid.

RNA consists of a chain of linked units called nucleotides. This disclosure relates mostly to RNA and, therefore, unless otherwise specified, the nucleotides and bases expressed refers to the ribo form of the nucleotide or base (i.e., ribonucleotide with one or more phosphate groups). Therefore "A" refers to rA or adenine, "U" refers to rU or uracil, "C" refers to rC or cytosine, "G" refers to rG or guanine, "I" refers to rI or inosine, "rN" refers to rA, rU, rC, rG or rI. Each of these (i.e., A, U, C, G, I) may have one or more phosphate groups as discussed above depending on whether they are part of a chain (i.e., RNA) or free (nucleoside, nucleotide, etc.).

"n" is a positive number and refers to the length of a ssRNA or dsRNA or to the average length of a population of ssRNA or dsRNA. "n" can be a positive integer when referring to one nucleic acid molecule or it can be any positive number when it is an average length of a population of nucleic acid molecules.

Single-stranded RNA or double-stranded RNA, may have a ratio of nucleotides or bases. For example, $r(C_{12}U)_n$ denotes a single RNA strand that has, on average 12 C bases or nucleotides for every U base or nucleotide. As another example, $r(C_{11-14}U)_n$ denotes a single RNA strand that has, on average 11 to 14 C bases or nucleotides for every U base or nucleotide. As another example, the formula "$rI_n \cdot r(C_{11-14}U)_n$" refers to a double-stranded RNA, one strand is poly(I) and the second strand is $r(C_{11-14}U)_n$.

As an example, the formula "$rI_n \cdot r(C_{12}U)_n$" can be expressed as "$riboI_n \cdot ribo(C_{12}U)_n$", "$rI_n \cdot ribo(C_{12}U)_n$", or "$riboI_n \cdot r(C_{12}U)_n$". It refers to a double-stranded RNA with two strands. One strand ($rI_n$) is poly ribo-inosine of n bases in length. The other strand is ssRNA with a ratio of C bases to U bases of 12 (i.e., 12 C/1 U=12) or about 12. While the ratio of C bases and U bases are defined as 12, the actual sequence is random.

The "·" symbol indicates that one strand of the dsRNA is hybridized (hydrogen-bonded) to the second strand of the same dsRNA. Therefore, $rI_n \cdot r(C_{12}U)_n$ is double-stranded RNA comprising two ssRNA. One ssRNA is poly(I) (or $rI_n$) and the other ssRNA is poly($C_{12}U$) (or $r(C_{12}U)_n$). It should be noted that while it is discussed in this disclosure that two strands are being hybridized, not 100% of the bases are hybridized (i.e., form base pairing) as some bases are mismatched. Also, because rU does not form base pairing with rI as well as rC form base paring with rI, rU provides a focus of hydrodynamic instability in $rI_n \cdot r(C_{12}U)_n$ at the locations of the U bases.

As discussed earlier, the term "r" and "ribo" has the same meaning in the formulas of the disclosure. Thus, as an example, rI, riboI, r(I), and ribo(I) refer to the same chemical which is the ribose form of inosine. Similarly, rC, riboC, r(C), and ribo(C) all refer to cytidine in the ribose form which is a building block of RNA. rU, riboU, r(U) and ribo(U) all refer to uracil in the ribose form, which is a building block of RNA.

In this disclosure, inosine is also considered a possible rNMP, rNDP or rNTP. Inosine is a nucleoside that is formed when hypoxanthine is attached to a ribose ring (also known as a ribofuranose) via a β-N9-glycosidic bond.

In some embodiments, the tdsRNA may comprises between 0.1% to 4% ssRNA, between 0.5% to 3% ssRNA, and between 1.5% to 2.5% ssRNA.

While this disclosure refers to dsRNA and tdsRNA, it is not required that the tdsRNA comprising only two ssRNA in duplex. For example, tdsRNA may comprise one strand of 300 bases and (1) two opposite strands of 150 bases each, or three opposite strands of 100 bases each.

The dsRNA (tdsRNA) and ssRNA of this disclosure are different and distinct from mRNA. For example, the ssRNA and dsRNA (tdsRNA) of this disclosure are preferably missing one or all of the following which are associated with mRNA: (1) 5' cap addition, (2) polyadenylation, (3) start codon, (4) stop codon, (6) heterogeneous protein-coding sequences, and (5) spice signals.

The terms "intranasal" or "intranasally," "instillation," "instillation of a liquid," "instillation using a sprayer" as used herein, refers to a route of delivery of an active compound to a patient by inhalation to the nasal mucosa, the airway, the lung or a combination thereof. Inhalation may be by breathing through the mouth or through a stoma as a result of a tracheostomy.

Active ingredients or active agents are used interchangeably and include any active ingredient or active agent described in this disclosure including, at least, tdsRNA. Other active agents include, at least, interferons such as Alferon.

2. tdsRNA

The double-stranded RNAs described in this disclosure are therapeutic double-stranded RNA, abbreviated as "tdsRNA." tdsRNA includes, at least, AMPLIGEN® (rintatolimod, which is a tdsRNA of the formula $rI_n \cdot r(C_{12}U)_n$). tdsRNA may be stored or administered in a pharmaceutically acceptable solution such as Phosphate Buffered Saline (PBS).

The tdsRNA may be a tdsRNA produced by any of the methods of this disclosure—referred to herein as the "tdsRNA Product" or "tdsRNA"—the two terms have the same meaning. tdsRNA can be represented by one or more of the formulas below in any combination:

$rI_n \cdot r(C_xU)_n$ (formula 1 which comprises AMPLIGEN®)

$rI_n \cdot r(C_xG)_n$ (formula 2)

$rA_n \cdot rU_n$ (also called polyA·polyU) (formula 3)

$rI_n \cdot rC_n$. (formula 4)

rugged dsRNA (formula 5)

Each will be discussed further below.

The tdsRNA may be represented by one or more of the formulas as follows:

$rI_n \cdot r(C_xU)_n$ (formula 1)

$rI_n \cdot r(C_xG)_n$ (formula 2)

Formula 1 comprises, at least, AMPLIGEN®.

x may be at least one selected from the group consisting of: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 4-29 (4 to 29), 4-30 (4 to 30), 4-35 (4 to 35), 11-14 (11 to 14), 30-35 (30 to 35). Of these, x=12, and x=11-14 are especially preferred.

In these formulas 1 to 5, and in other formulas, where there is no subscript next to a base, the default value is "1." For example, in the formula $rI_n \cdot r(C_{12}U)_n$, there is no subscript following "U," it is understood that $rI_n \cdot r(C_{12}U)_n$ is the same as $rI_n \cdot r(C_{12}U_1)_n$, and the formula is meant to convey that for the strand denoted as $r(C_{12}U_1)_n$, there are 12 rC base for every rU base. Thus, x is also a ratio of the bases of one strand of the tdsRNA. The length of the tdsRNA strand is denoted as a lowercase "n" (e.g., $rI_n \cdot r(C_{12}U)_n$). The subscript n is also the length of each individual single stranded nucleic acid. Since tdsRNA is double stranded, n is also the length of the double stranded nucleic acid—i.e., the length of the tdsRNA. For example, $rI_n \cdot r(C_{12}U)_n$ in intended to indicate, inter alia, a double stranded RNA with each strand with a length of n.

In another aspect, the tdsRNA may have a formula as follows:

$rA_n \cdot rU_n$ (also called polyA·polyU) (formula 3)

$rI_n \cdot rC_n$. (formula 4)

In another aspect, the tdsRNA may be a rugged dsRNA (formula 5).

In one embodiment, tdsRNA is one or more selected from the group consisting of formula 1, formula 2, formula 3, formula 4, and formula 5. In another embodiment, tdsRNA comprises formula 1 and formula 2 only. In one preferred embodiment, tdsRNA comprises formula 1 only. In another embodiment, tdsRNA comprises formula 1 and formula 5 (rugged dsRNA) only.

In another aspect, at least 70%, at least 80%, or at least 90% of the tdsRNA may have a molecular weight of between 400,000 Daltons to 2,500,000 Daltons. Where the term percent ("%") is used, the percent may be weight percent or molar percent.

In another aspect, the tdsRNA comprises a first ssRNA and a second ssRNA and each of these first ssRNA or second ssRNA may contain one or more strand breaks.

In another aspect, the tdsRNA may comprise at least one selected from the group consisting of: a 3' overhang end, a 5' overhang end, a blunt end, an internal ssRNA sequence, one or more strand breaks in a first ssRNA, and one or more strand breaks in a second ssRNA.

In another aspect, the tdsRNA is a linear molecule—that is a molecule that is not branched or that does not contain any loop structure. In different aspects, at least 60%, at least 70%, at least 80%, at least 90%, at least 95% or 100% of the tdsRNA is a linear molecule.

In another aspect, the tdsRNA has the property that greater than about 90%, greater than 95%, greater than 98%, greater than 99%, or 100% of the bases of the RNA are in a double-stranded configuration.

In any aspect, the tdsRNA may be in a therapeutic composition comprising, for example, a tdsRNA, and a pharmaceutically acceptable excipient.

One embodiment of tdsRNA is directed to rintatolimod, which is a tdsRNA of the formula $rI_n \cdot r(C_{12}U)_n$ and which is also denoted by the trademark AMPLIGEN®.

In a preferred embodiment, the tdsRNA are of the general formula $rI_n \cdot r(C_{11-14}, U)_n$ and are described in U.S. Pat. Nos. 4,024,222 and 4,130,641 (which are incorporated by reference herein) or synthesized according to this disclosure.

In the case where the tdsRNA is $rA_n \cdot rU_n$, the tdsRNA may be matched (i.e., not in mismatched form).

tdsRNA (e.g., AMPLIGEN®) has undergone extensive clinical and preclinical testing. It has been generally well-tolerated in clinical trials enrolling over 1,200 patients with over 100,000 doses administered and there have been no drug-related deaths. Two placebo-controlled, randomized studies show no increase in serious adverse events compared to placebo. Favorable safety profiles have been seen for intraperitoneal, intravenous, and intranasal routes of administration of tdsRNA.

2.1 Length of tdsRNA

The length of the tdsRNA, may be represented by bases for one strand of the tdsRNA or in basepairs for both strands for the tdsRNA. It is understood that in some embodiments that not all of the bases (e.g., U and I) are in basepaired configuration. For example, rU bases do not pair as well as rC bases to inosine.

The length of the tdsRNA may be measured by (1) bases or basepairs, (2) molecular weight which is the weight of the double stranded tdsRNA (e.g., Daltons) or (3) turns of the double stranded RNA. These measurements can be easily interconverted. For example, it is generally accepted that there are about 629 Daltons per base pair.

"n" represents length in units of basepair or basepairs (abbreviated as bp regardless of whether it is singular or plural) for double stranded nucleic acid. "n" can also represent bases for single stranded RNA. Because "bp" represents singular or plural, it is the same as "bps" which is another representation of basepairs.

The tdsRNA can have the following values for its length "n" (in bases for single strand or basepairs for double strands): 4-5000, 10-50, 10-500, 10-40,000, 40-40,000, 40-50,000, 40-500, 50-500, 100-500, 380-450, 400-430, 400-800 or a combination thereof. Expressed in molecular weight, the tdsRNA may have the following values: 30 kDa to 300 kDa, 250 kDa to 320 kDa, 270 kDa to 300 kDa or a combination thereof. Expressed in helical turns, the tdsRNA may have 4.7 to 46.7 helical turns of duplexed RNA, 30 to 38 helical turns of duplexed RNA, 32 to 36 helical turns of duplexed RNA or a combination thereof.

The length may be an average basepair, average molecular weight, or an average helical turns of duplexed RNA and can take on integer or fractional values.

2.2 Rugged dsRNA (a Form of tdsRNA

Rugged dsRNA is a tdsRNA that is resistant to denaturation under conditions that are able to separate hybridized poly(riboinosinic acid) and poly(ribocytosinic acid) strands (that is, $rI_n \cdot rC_n$ strands). See, U.S. Pat. Nos. 8,722,874 and 9,315,538 (incorporated by reference) for a further description of Rugged dsRNA and exemplary methods of preparing such molecules.

In one aspect, a rugged dsRNA can be an isolated double-stranded ribonucleic acid (dsRNA) which is resistant to denaturation under conditions that are able to separate hybridized poly(riboinosinic acid) and poly(ribocytosinic acid) strands, wherein only a single strand of said isolated dsRNA comprises one or more uracil or guanine bases that are not base-paired to an opposite strand and wherein said single strand is comprised of poly(ribocytosinic$_{30-35}$uracilic acid). Further, the single strand may be partially hybridized to an opposite strand comprised of poly(riboinosinic acid). In another aspect, rugged dsRNA may be an isolated double-stranded ribonucleic acid (dsRNA) which is resistant to denaturation under conditions that are able to separate hybridized poly(riboinosinic acid) and poly(ribocytosinic acid) strands.

In another aspect, Rugged dsRNA, has at least one of the following: $r(I_n) \cdot r(C_{4-29}U)_n$, $r(I_n) \cdot r(C_{12}U)_n$, $r(I_n) \cdot r(C_{11-14}U)_n$, $r(I_n) \cdot r(C_{30}U)_n$, or $r(I_n) \cdot r(C_{30-35}U)_n$. In another aspect, Rugged dsRNA may have a size of 4 bps to 5000 bps, 40 bps to 500 bps, 50 bps to 500 bps, 380 bps to 450 bps, 400 bps to 430 bps, 30 kDa to 300 kDa molecular weight, 250 kDa to 320 kDa molecular weight, 270 kDa to 300 kDa molecular weight, 4.7 to 46.7 helical turns of duplexed RNA, 30 to 38 helical turns of duplexed RNA, 32 to 36 helical turns of duplexed RNA, and a combination thereof.

In another aspect, Rugged dsRNA is produced by isolating the 5 minute HPLC peak of a tdsRNA preparation.

2.3 Rugged dsRNA Preparation

In one embodiment, the starting material for making Rugged dsRNA may be dsRNA prepared in vitro using conditions of this disclosure. For example, the specifically configured dsRNA described in U.S. Pat. Nos. 4,024,222, 4,130,641, and 5,258,369 (which are incorporated by reference herein) are generally suitable as starting materials after selection for rugged dsRNA. tdsRNA (or preparations of tdsRNA) described in this disclosure is also useful as starting material.

After procuring starting material, Rugged dsRNA may be isolated by at least subjecting the partially hybridized strands of a population of dsRNA to conditions that denature most dsRNA (more than 10 wt % or mol %, more than 20 wt % or mol %, more than 30 wt % or mol %, more than 40 wt % or mol %, more than 50 wt % or mol %, more than 60 wt % or mol %, more than 70 wt % or mol %, more than 80 wt % or mol %, more than 90 wt % or mol %, more than 95 wt % or mol %, or more than 98 wt % or mol %) in the population, and then selection negatively or positively (or both) for dsRNA that remain partially hybridized. The denaturing conditions to unfold at least partially hybridized strands of dsRNA may comprise an appropriate choice of buffer salts, pH, solvent, temperature, or any combination thereof. Conditions may be empirically determined by observation of the unfolding or melting of the duplex strands of ribonucleic acid. The yield of rugged dsRNA may be improved by partial hydrolysis of longer strands of ribonucleic acid, then selection of (partially) hybridized stands of appropriate size and resistance to denaturation.

The purity of rugged dsRNA, which functions as tdsRNA, may thus be increased from less than about 0.1-10 mol % (e.g., rugged dsRNA is present in at least 0.1 mol % or 0.1 wt percent but less than about 10 mol % or 10 wt percent) relative to all RNA in the population after synthesis to a higher purity. A higher purity may be more than 20 wt % or mol %, more than 30 wt % or mol %, more than 40 wt % or mol %, more than 50 wt % or mol %, more than 60 wt % or mol %, more than 70 wt % or mol %, more than 80 wt % or mol %, more than 90 wt % or mol %, more than 98 wt % or mol %, or between 80 to 98 wt % or mol %. All wt % or mol % is relative to all RNA present in the same composition.

Another method of isolating Rugged dsRNA is to employ chromatography. Under analytical or preparative high-performance liquid chromatography, Rugged dsRNA can be isolated from a preparation (e.g., the starting material as described above) to produce poly(I):poly($C_{12}U)_n$ (e.g., poly (I):poly($C_{11-14}U)_n$) as a substantially purified and pharmaceutically-active molecule with an HPLC peak of about 4.5 to 6.5 minutes, preferably between 4.5 and 6 minutes and most preferably 5 minutes.

Rugged dsRNA and the method of making rugged dsRNA are described in U.S. Pat. Nos. 8,722,874 and 9,315,538 (incorporated by reference).

2.4 Stabilizing Polymers

In any of the described embodiments, the tdsRNA may be complexed with a stabilizing polymer such as: polylysine, polylysine plus carboxymethylcellulose (lysine carboxy methyl cellulose), polyarginine, polyarginine plus carboxymethylcellulose, or a combination thereof. Some of these stabilizing polymers are described, for example, in U.S. Pat. No. 7,439,349.

2.5 Modified Backbone

The tdsRNA may comprise one or more alterations in the backbone of the nucleic acid. For example, configured tdsRNA may be made by modifying the ribosyl backbone of poly(riboinosinic acid) $r(I_n)$, for example, by including 2'-O-methylribosyl residues. Specifically configured dsRNA may also be modified at the molecule's ends to add a hinge(s) to prevent slippage of the base pairs, thereby conferring specific bioactivity in solvents or aqueous environments that exist in human biological fluids.

3. Interferons

One optional component of the composition is interferon. As used herein, the term "interferon" (abbreviated "IFN") refers collectively to type 1 and type 2 interferons and including deletion, insertion, or substitution variants thereof, biologically active fragments thereof, and allelic forms thereof. As used herein, interferon refers collectively to type 1 and type 2 interferons. Type 1 interferon includes interferons alpha, beta, omega and their subtypes. Human interferon alpha has at least 14 identified subtypes while interferon beta has 3 identified subtypes.

The interferon may be at least one selected from the group consisting of: interferon, interferon mixture, Alferon, alpha-interferon species, recombinant or natural interferon alpha, recombinant or natural interferon alpha 2a, recombinant or natural interferon beta, recombinant or natural interferon beta 1b, recombinant, and natural interferon gamma.

The interferon is optionally an alpha-interferon. One preferred alpha interferon is ALFERON N Injection® the only approved natural, multi-species, α-interferon available in the United States. It is the first natural source, multi-species interferon and is a consistent mixture of at least seven species of α-interferon. The interferon is preferably a natural cocktail of at least seven species of human α-interferon. In contrast, the other available α-interferons are single molecular species of α-interferon made in bacteria using DNA recombinant technology. These single molecular species of α-interferon also lack an important structural carbohydrate component because this glycosylation step is not performed during the bacterial process.

Unlike species of α-interferon produced by recombinant techniques, ALFERON N Injection® is produced by human white blood cells that are able to glycosylate the multiple α-interferon species. Reverse phase HPLC studies show that ALFERON N Injection® is a consistent mixture of at least seven species of alpha interferon (α2, α4, α7, α8, α10, α16 and α17). This natural-source interferon has unique antiviral properties distinguishing it from genetically engineered interferons. The high purity of ALFERON N Injection® and its advantage as a natural mixture of seven interferon species, some of which, like species 8b, have greater antiviral activities than other species, for example, species 2b, which is the only component of INTRON A®. The superior antiviral activities, for example, in the treatment of chronic hepatitis C virus (HCV) and HIV infection, and tolerability of ALFERON N Injection® compared to other available recombinant interferons, such as INTRON A® and ROFERON A®, have been reported. ALFERON N Injection® is available as an injectable solution containing 5,000,000 international units (IU) per ml.

The interferon may be interferon species purified as a mixture of at least seven species of alpha-interferon produced by human white blood cells. The seven species may be, for example, interferon alpha 2; interferon alpha 4; interferon alpha 7; interferon alpha 8; interferon alpha 10; interferon alpha 16; and interferon alpha 17.

For internal or any administration, the α-interferon may, for example, be formulated in conventional manner for oral, nasal or buccal administration. Formulations for oral administration include aqueous solutions, syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents. α-Interferon may be administered by any method of administration of this disclosure. Preferably administration is by a suitable route including oral, nasal, parenteral (including injection) or topical (including transdermal, buccal and sublingual). It will be appreciated that the preferred route will vary with the condition and age of the recipient, the nature and severity of endometriosis and chosen tdsRNA.

The recommended dosage of the components will depend on the clinical status of the patient and the experience of the clinician in treating similar conditions. As a general guideline, a dosage of ALFERON N Injection® utilized for systemic infections is 3 IU/pound to 10 million IU/pound (e.g., subcutaneous injection) three times weekly. Experience to date is with dosages above 3 IU/lb of patient body weight. Oral α-interferon (ALFERON LDO®) has been administered as a liquid solution in the range of 500-10,000 IU/day and calculated on the basis of a 150 pound human this is from 3.3 to 66.0 IU/lb per day. In one preferred embodiment, beneficial results are obtained at dosage levels of α-interferon in excess of 450 IU, that is greater than 3 IU/pound body weight. A healthcare provider would be able, however, to determine the optimal dose and schedule of low dose oral α-interferon (or any interferon) to achieve a desired antiviral effect.

4. Administration (Delivery

The methods of the disclosure are useful for treating a subject in need thereof. A subject in need thereof is a subject having or at risk of having endometriosis. In its broadest sense, the terms "treatment" or "to treat" refer to both therapeutic and prophylactic treatments. If the subject in need of treatment is one who is at risk of having endometriosis, then treating the subject refers to decrease the likelihood that the subject will develop endometriosis, as well as to a treatment after the subject has developed endometriosis in order to reduce or eliminate it altogether or prevent it from becoming worse. A patient at risk would include, at least, a patient who has previously developed endometriosis.

4.1 Administration Route

In a preferred embodiment, all of this disclosure (administrations, formulations, medicaments, dosages) relates to and describes at least to their application to a human female of reproductive age (between menarche and menopause).

The pharmaceutical composition comprising one or more active agents (e.g., tdsRNA) of this disclosure may be administered to a subject by any local or systemic route or method known in the art. The preferred route may vary with the age, condition, gender, or health status of the subject; the nature of the disease, the number and severity of symptoms, chosen active ingredient, or the presence of other pathological conditions.

The most preferred methods include intravenous administration; intraperitoneal administration; or intranasal administration (including e.g., breathing through the mouth or airway—e.g., through a stoma made by tracheostomy). Intravenous administration or intraperitoneal administration is commonly performed with a needle. Other administration methods include, at least, intradermal administration; subcutaneous administration; intramuscular administration; intraperitoneal administration; intracranial administration; intravesical administration; oral administration (through the mouth, by breathing through the mouth); topical administration; inhalation administration; aerosol administration; intra-airway administration; tracheal administration; bronchial administration; instillation administration; bronchoscopic instillation administration; intratracheal administration; mucosal administration; dry powder administration; spray administration; contact administration; swab administration; intratracheal deposition administration; intrabronchial deposition administration; bronchoscopic deposition administration; lung administration; nasal passage administration; respirable solid administration; respirable liquid administration; dry powder inhalants administration; and a combination thereof. It is noted where more than one active ingredient (e.g., different tdsRNAs, interferon, etc) is administered, the active ingredients may be administered by the same route or different routes and may be administered by different route.

Some forms of administration (administering) may be described by one or more of the above categories and some administration methods may be grouped differently or may be referred to by broader terms. For example, enteral administration may refer to oral administration, feeding tube administration, or enema administration; topical administration may be by a device such as a nebulizer for inhalation through the respiratory system, by skin patch acting epicutaneously or transdermally, or by suppository acting in the rectum or vagina. Parenteral administration may take the form of subcutaneous administration, intravenous administration, intramuscular administration, intradermal administration, or intraperitoneal administration; buccal administration, sublingual administration, transmucosal administration; inhalation administration, instillation administration, instillation administration, intranasally administration, instillation administration. intratracheal administration.

Nasal administration refers to any administration through the airway and is another term for pulmonary airway administration. Nasal administration may include administration to the airway through the mouth (i.e., through breathing through the mouth or through a stoma made by tracheostomy).

Nasal administration includes administration to a tissue of the airway. This includes a tissue selected from the group consisting of: an airway tissue; nose tissue; oral tissue; alveoli tissue; pharynx tissue; trachea tissue; bronchi tissue; carina tissue; bronchi tissue; bronchioles tissue; lung tissue; tissue in the lobe of a lung; alveoli tissue; nasal passage tissue; nasal epithelium tissue; larynx tissue; bronchi tissue; inhalation tissue; and a combination thereof. It follows that nasal administration may include administration to cells and tissues such as: an epithelium cell; an airway epithelium cell; a ciliated cell; a goblet cell; a non-ciliated cell; a basal cell; a lung cell; a nasal cell; a tracheal cell; a bronchial cell; a bronchiolar epithelial cell; an alveolar epithelial cell; a sinus cell; and a combination thereof.

Administration may be from any known delivery system. A delivery system may be selected from the group consisting of: a pill, a capsule, a needle, a cannula, an implantable drug depot, an infusion system (e.g., a device similar to an insulin pump); a nebulizer; a sprayer; a nasal pump; a squeeze bottle; a nasal spray; a syringe sprayer, a plunger sprayer (a syringe providing pressure to an attached sprayer or nozzle); a nasal aerosol device; a controlled particle dispersion device; a nasal aerosol device; a nasal nebulization device; a pressure-driven jet nebulizer; an ultrasonic nebulizer; a breath-powered nasal delivery device; an atomized nasal medication device; an inhaler; a powder dispenser; a dry powder generator; an aerosolizer; an intrapulmonary aerosolizer; a sub-miniature aerosolizer; a propellant based metered-dose inhalers; a dry powder inhalation devices; an instillation device; an intranasal instillation device; an intravesical instillation device; a swab; a pipette; a nasal irrigation device; a nasal rinse; an aerosol device; a metered aerosol device; a pressurized dosage device; a powdered aerosol; a spray aerosol; a spray device; a metered spray device; a suspension spray device; and a combination thereof.

4.2 Administration Formulations

Formulations for administration (i.e., pharmaceutical compositions) may include pharmaceutically acceptable carrier with the active ingredient or agent.

Pharmaceutical carriers include suitable non-toxic vehicles in which a composition of the disclosure is dissolved, dispersed, impregnated, or suspended, such as water or other solvents, fatty materials, celluloses and their derivatives, proteins and their derivatives, collagens, gelatine, polymers, adhesives, sponges, fabrics, and the like and excipients which are added to provide better solubility or dispersion of the drug in the vehicle. Such excipients may include non-toxic surfactants, solubilizers, emulsifiers, chelating agents, binding materials, lubricants softening agents, and the like. Pharmaceutically acceptable carriers may be, for example, aqueous solutions, syrups, elixirs, powders, granules, tablets, and capsules which typically contain conventional excipients such as binding agents, fillers, lubricants, disintegrants, wetting agents, suspending agents, emulsifying agents, preservatives, buffer salts, flavoring, coloring, and/or sweetening agents.

Unless otherwise indicated, all percentages (%) of ingredients are meant to represent weight percent (wt %) or mole percent. Where nucleic acid (e.g., RNA) is not involved, wt % is preferred.

The liquid carrier may be water or any other suitable liquid, solvent, or mixture thereof. One preferred liquid carrier may be phosphate buffered saline.

The liquid compositions of this disclosure are particularly suited for nasal administration.

4.3 Medicament

In another aspect, a medicament (e.g., a pharmaceutical composition) containing the tdsRNA is provided. Optional other components of the medicament include excipients and a vehicle (e.g., aqueous buffer or water for injection) packaged aseptically in one or more separate containers (e.g., nasal applicator or injection vial). Further aspects will be apparent from the disclosure and claims herein.

5. Dosage for the Average Subject

The dosages is generally applicable to a subject as described in another section of this disclosure. In a preferred embodiment, the subject is a human female of reproductive age (between menarche and menopause).

For a subject the dose of tdsRNA per day may be at least one selected from the group consisting of: 0.1 µg to 1,000,000 µg, 0.1 µg to 25,000 µg, 0.4 to 400,000 µg, 0.5 µg to 5,000 µg, 0.5 mg to 60 mg, 5 mg to 40 mg, 5 mg to 400 mg, 10 mg to 20 mg, 10 mg to 800 mg, 25 mg to 700 mg, 20 mg to 200 mg, 50 mg to 150 mg, 80 mg to 140 mg, and a combination thereof.

A subject may be a human of about 150 lb or 70 Kg in weight and the appropriate dosage per body weight may be calculated.

5.1 Dose in Kilogram Per Day

In another aspect, the tdsRNA is administered in a dose per day selected from the group consisting of 0.1 mg/kg, 0.2 mg/kg, 0.3 mg/kg, 0.5 mg/kg, 0.7 mg/kg, 0.8 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 0.1-1 mg/kg, 0.1-2 mg/kg, 0.1-3 mg/kg, 0.1-4 mg/kg, 0.1-5 mg/kg, 0.1-6 mg/kg, 0.1-7 mg/kg, 0.1-8 mg/kg, 0.1-10 mg/kg, 0.1-20 mg/kg, 0.2-3 mg/kg, 0.3-3 mg/kg, 0.4-3 mg/kg, 0.6-3 mg/kg, and 0.8-3 mg/kg.

5.2 Amount Per Unit Dose

The amount per unit dose of tdsRNA may be at least one selected from 0.1 mg/kg, 0.2 mg/kg, 0.4 mg/kg, 0.6 mg/kg, 0.8 mg/kg, 1 mg/kg, 2 mg/kg, 3 mg/kg, 4 mg/kg, or 5 mg/kg.

5.3 Specific Examples

In one embodiment, the tdsRNA is administered at a dose from about 1 mg/kg to 10 mg/kg biweekly. As another example, the administration may be in 50-1400 milligrams every other day leading to an average daily dosage of 25-700 milligrams per day. In one embodiment, the tdsRNA is administered at a dose from about 0.50 mg/kg to 10 mg/kg every other week. 50-1400 milligrams every other day leading to an average daily dosage of 25-700 milligrams per day.

5.4 Dose Frequency

In certain embodiments, the tdsRNA is administered at a frequency selected from the group consisting of: one dose per day, one dose every 2 days, one dose every 3 days, one dose every 4 days, one dose every 5 days, 4 doses a week, 3 doses a week, 2 doses a week, 1 dose a week, one dose every two weeks, one dose every three weeks, one dose every four weeks, and one dose every month.

5.5 Number of Doses and Dosing Period

In certain embodiments, the tdsRNA is administered as a single dose, in two doses, in three doses, in four doses, in five doses, or in 6 or more doses. In other embodiments, the dosage is continued indefinitely. Continuous dosage may be used under some circumstances, for example, if the subject is already using an insulin pump the tdsRNA may be admixed with the insulin.

A dosing period is usually about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In certain embodiments, multiple (for example, 2, 3, 4, 5, 6, 7, 8, 9, 10 or more) doses of a tdsRNA are administered to a subject in need of treatment. As discussed, for a subject with recurrent endometriosis, the dosing period may be continuous without end.

5.6 Nasal Dosage tdsRNA may be administered at the same dose in nasal administration as for any other form of administration. Nonlimiting specific examples of nasal administration (which is also applicable for any other form of administration) include: a dose of 5 µg to 10 µg; 10 µg to 20 µg; 20 µg to 50 µg; 50 µg to 100 µg; 100 µg to 200 µg; 200 µg to 500 µg; 500 µg to 1000 µg; 1000 µg to 1500 µg; 1500 µg to 2000 µg; or any combination thereof.

Unless otherwise specified, "composition," "a composition," or "the composition" includes, at least, a composition of the disclosure or includes at least tdsRNA. Compositions may be optionally filtered and sterilized to enhance safety, stability and solubility. The composition may be formulated to enhance the delivery method. For example, the formulation may be formulated to enhance intraperitoneal delivery or nasal delivery.

6. Other Embodiments and Features

6.1 Subject or Patient

As used herein, the terms "patient" or "subject" are used interchangeably. In this disclosure, the subject is preferably a female mammal. Preferably the subject is a female human. Most preferably, the subject is a human female of reproductive age (between menarche and menopause).

It is understood that where the subject is not specified, the subject is one of the preferred subjected listed above.

6.2 Devices and Kits

In another aspect, the present disclosure relates to and comprises a therapeutic device for intranasal delivery. In one embodiment, the therapeutic device may comprise any suitable devices charged with a preparation of the compositions of this disclosure (tdsRNA). These devices are described in more detail below.

6.3 Effective Amount: Therapeutically or Prophylactically Effective Amount

The compositions are delivered in effective amounts. The term "effective amount" refers to the amount necessary or sufficient to realize a desired biologic effect. Combined with the teachings provided herein, by choosing among the various active compounds and weighing factors such as potency, relative bioavailability, patient body weight, severity of adverse side effects and preferred mode of administration, an effective prophylactic or therapeutic treatment regimen can be planned which does not cause substantial toxicity and yet is effective to treat the particular subject to effectively preventing, treating, inhibiting, or attenuating an Endometriosis.

One of ordinary skill in the art can empirically determine the effective amount of a particular active ingredient without necessitating undue experimentation.

6.4 General Discussion

It should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity that a person skilled in the art would understand does not affect the operation of the disclosure or its patentability.

All modifications and substitutions that come within the meaning of the claims and the range of their legal equivalents are to be embraced within their scope. Different scopes of each embodiment or claim are envisioned. Thus, the terms "comprising," "consisting essentially of," and "consisting of" can be used to claim the disclosure.

It should be understood that an element described in this specification should not be construed as a limitation of the claimed disclosure unless it is explicitly recited in the claims. Thus, the granted claims are the basis for determining the scope of legal protection instead of a limitation from the specification which is read into the claims. In contradistinction, the prior art is explicitly excluded from the disclosure to the extent of specific embodiments that would anticipate the claimed disclosure or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the disclosure. Similarly, generalizations of the disclosure's description are considered to be part of the disclosure.

From the foregoing, it would be apparent to a person of skill in this art that the disclosure can be embodied in other specific forms without departing from its spirit or essential characteristics. While the disclosure has been described in connection with what is presently considered to be the most practical and preferred embodiment, it is to be understood that the disclosure is not to be limited to the disclosed embodiment, but on the contrary, is intended to cover various modifications and equivalent arrangements included within the spirit and scope of the appended claims.

INCORPORATION BY REFERENCE

All publications, patent applications, and patents mentioned herein are hereby incorporated by reference in their entirety as if each individual publication or patent was specifically and individually indicated to be incorporated by reference. These patents include, at least, U.S. Pat. Nos. 4,024,222, 4,130,641, 5,258,369, 7,439,349, 8,722,874 and 9,315,538. In case of conflict, the present application, including any definitions herein, will control.

EXAMPLES

Example 1: Production of a dsRNA which is One Aspect of a Therapeutic dsRNA

Disclosed herein is one method of producing tdsRNA. Synthesis of single-stranded poly(I) and poly($C_{12}U$) began with enzymatic polynucleotide synthesis of the polynucleotides from the respective nucleotides starting materials: inosine for poly(I); cytidine (C) and uridine (U) for poly($C_{12}U$). Then repetitive extraction and precipitation steps were used to remove residual impurities. The reaction solutions containing the products were concentrated by ultrafiltration and extracted with phenol four times. The concentrated and extracted solutions were precipitated, dissolved, and re-precipitated from aqueous ethanol (50:50). Whereas precipitated poly(I) was separated by centrifugation, the supernatant (waste) liquid phase of adherent poly($C_{12}U$) was simply removed by aspiration. The precipitated pastes were re-dissolved, then concentrated, diafiltered, and further concentrated. The final bulk solutions containing polynucleotide was filtered. The filtered solution was freeze-dried, and the raw materials were stored frozen.

Enzymatic Synthesis. The enzymatic synthesis used in the manufacturing process is dependent on the enzyme polynucleotide phosphorylase to synthesize polyinosinic acid and polycytidilic$_{12}$uridilic acid from their respective starting materials: cytidine 5'-diphosphate, trisodium salt (CDP·$Na_3$), uridine 5'-diphosphate, disodium salt (UDP·$Na_2$) and inosine 5' diphosphate, trisodium salt (IDP·$Na_3$).

The enzyme catalyzes polynucleotide formation in a reversible reaction using Mg' as a co-factor. Polynucleotides were synthesized in the 5' to 3' direction with concurrent liberation of inorganic phosphate. The maximum yield was limited by the equilibrium between synthesis and reverse rates, degradative reaction (phosphorolysis). The progress of the reaction was followed by measuring the consumption of CDP or IDP. The viscosity of the reaction solution was also monitored. Purified water was filtered into the tank. The following ingredients were added to the tank one at a time with mixing: TRIS (hydroxymethyl) aminomethane, urea, magnesium chloride hexahydrate (MgCl·6H$_2$O), and ethylenediaminetetraacetic acid (edetate), disodium salt (EDTA·Na$_2$). Raw material mononucleotides were also added.

Each ingredient was dissolved before the next one was added. After all of the ingredients were added, the solution was mixed for a minimum of 10 minutes. The mixture was then adjusted and purified water was added to obtain a final batch volume. This pre-enzyme reaction mixture was sampled for initial CDP or IDP concentration. The enzyme polynucleotide phosphorylase was added with mixing, whereupon the synthesis of polynucleotide commenced. Also, the viscosity profile at the optimal enzyme concentration must exhibit the usual increase in viscosity over time without a significant decrease at the conclusion of the batch reaction; a significant decrease in viscosity would indicate undesired degradation of polynucleotide. After the optimized amount of enzyme was added to the production batch, enzymatic synthesis progressed under constant, controlled agitation. The consumption of CDP or IDP was monitored approximately every hour. The reaction was terminated by the addition of a stop solution. Viscosity was also monitored, for information only, during the process.

Concentration of Reaction Solution. To minimize the required volume of phenol for extractions, the reaction product solution was concentrated.

Extraction of dsRNA mixture. The residual enzyme was removed predominately by phenol extraction. The concentrated single stranded RNA reaction product solutions were transferred into separate extraction tanks and 2M TRIS and sodium dodecyl sulfate (SDS) were added. After at least 5 minutes of mixing, liquefied phenol was added and the two-phase solution was mixed to disperse the phenol phase in the aqueous phase. SDS was employed as a surface-active agent to facilitate the dissolution of denatured protein into the phenol phase; TRIS was required to buffer the solution at an optimal pH for polynucleotide stability. The extraction mixture stands without mixing for pre-determined settling times to afford the coalescence of the phases. The lower phenol waste phase is then pumped into containers for disposal. The location of the phenol cut was important in order to effectively separate phenol and protein from the upper, product phase, which contains single-stranded RNAs. The phenol phase and an intermediate "rag" layer, which contains denatured protein solids, were discarded by visually observing the liquid flowing through the site glass at the tank outlet. When the phenol and rag layer disappeared and only the product phase was observed, the outlet valve was closed and the phenol cut is considered complete.

Precipitation of single-stranded RNAs. Contaminating phenol, SDS, and other salts remaining in solution were removed by precipitation with denatured ethyl alcohol. The single-stranded RNA concentrated solution was pumped into the precipitation tank. The denatured alcohol was added and after mixing the precipitate was separated.

Concentration and Diafiltration. Remaining bulk salts, a small amount of unreacted mononucleotide, and phenol were removed by diafiltration against water. The precipitate was dissolved in the original precipitation vessel with gentle mixing and heating. After dissolving, the solution was then concentrated and diafiltered against water for injection (WFI).

Manufacture of dsRNA, Sterile Solution, for Intravenous Infusion. Equal molar amounts of the ssRNA were mixed in an annealing step, and cooled to room temperature. The solutions were sterile filtered.

Preparation of Buffer Vehicle, Excipient Solution. WFI was added to the tank. The excipients were added to the tank, and mixed. After mixing, the batch was sampled for pH and osmolality. Quality control must be within in-process limits prior to use for formulating the solutions.

Formulating Poly(I) and Poly(C$_{12}$U) solutions. An initial quantity of buffer solution was subdivided according to the batch formula and was filtered into the tank. The single-stranded RNAs were added to the buffer solution, and dissolved by mixing. The temperature of the solution was increased and maintained with mixing. The solution is then recirculated.

Annealing of Poly I:Poly C$_{12}$U Strands. Equivalent quantities of poly(I) and poly(C$_{12}$U) were transferred to the tank. With continual mixing, the temperature of the solution was increased. Samples were removed and tested for potency, and pH.

Sterile Filtration. The formulated bulk was sterile filtered in-line into a steam-sterilized surge vessel.

Filling Operations. The filling operation was performed. After each vial was filled, a sterile stopper is used to stopper the vial. Stoppered vials were then conveyed from the aseptic processing area where they were sealed.

Example 2: Production of Rugged RNA (Rugged dsRNA) which is One Aspect of a Therapeutic dsRNA Rugged dsRNA was produced from an annealed dsRNA mixture (i.e., tdsRNA). This mixture may be, for example, from the poly(I):poly(C$_{12}$U) mixture prepared according to the above (e.g., AMPLIGEN®) by either analytical or preparative high performance liquid chromatography (HPLC) as a substantially purified and pharmaceutically-active molecule. Its molecular weight is from about 30 kDa to 300 kDa and is about 50 to 500 base pairs in length with about 4.7 to 46.7 complete turns of the RNA helix. It is only from about 4 mol % to about 16 mol % of an unfractionated AMPLIGEN® composition.

Due to its structure, Rugged dsRNA is unusually resistant to disruption of its RNA double helix and molecular unfolding. Thus, Rugged dsRNA under the assay conditions described herein has about 100- to about 1,000% greater bioactivity than the same weight of unimproved AMPLIGEN® poly(I):poly(C$_{12}$U).

Stability of Rugged dsRNA. Stability of poly(I):poly(C$_{12}$U) was measured at an accelerated temperature condition of 40° C. as compared to the long-term storage temperature of from 2° C. to 8° C. The size of poly(I):poly(C$_{12}$U) decays at this temperature as measured by analytical ultracentrifugation (S$_{20,w}$). Decrease in size is due to unfolding of the double helix (loss of hydrogen bonds) and concurrent hydrolysis of the phosphodiester bonds. For bioactivity unimproved AMPLIGEN® (poly(I):poly(C$_{12}$U)) requires a sedimentation coefficient from about 10.0 to about 15.0 S$_{(20,w)}$, whereas the size of poly(I):poly(C$_{12}$U) at more than 180 days at 40° C. is about 8.0 S$_{(20,w)}$ and indicates a loss of bioactivity.

Other methods for producing tdsRNA are known. See, U.S. Pat. Nos. 8,722,874 and 9,315,538, which is incorporated by reference herein, for a further description of Rugged dsRNA and exemplary methods of preparing such molecules.

Example 3 tdsRNA Enhances NK Cell Activity and Macrophage Activity in the Peritoneal Cavity As discussed above, there are at least 3 defects that render a person more susceptible to endometriosis as follows:

1. decrease in macrophage activity;
2. decrease in NK cell activity; and
3. decrease in T effector cell/T regulatory cell ratio.

This example shows that tdsRNA augmented both peritoneal and systemic NK (Natural Killer) cell activity (see, e.g., Table 2 and Table 3); and peritoneal macrophage activity (see, e.g., Table 2). In these mouse experiments, AMPLIGEN® was administered intraperitoneally in a mouse model.

Briefly, B6C3F1 mice were injected IP with AMPLIGEN® at the indicated dose of AMPLIGEN® one day before measuring NK cell and macrophage activity. The results are expressed as the mean value±S.E.M. (Standard error of the mean) of triplicate determinations and are plotted in Table 2.

Example 4 AMPLIGEN® Enhances the Activity of Human NK Cells

The ability of AMPLIGEN® to augment natural killer cell cytotoxicity are shown in the experimental data presented in Table 3. Table 3 depicts data showing augmentation of natural killer (NK) cell activity (cytotoxicity) using peripheral blood mononuclear cells collected from 15 human patients with chronic fatigue syndrome (CFS).

The augmentation was seen at both effectors to target cell (K562) ratio utilized. If AMPLIGEN® had no effect, mean NK cell cytotoxicity would have been at 0%. Instead, mean NK cell cytotoxicity increased 178% at an E:T ratio of 12.5:1 and increased 75% at an E:T ratio of 25:1 showing that AMPLIGEN® clearly has a beneficial effect on augmenting natural killer cell cytotoxicity.

TABLE 3 tdsRNA Augmentation of Natural Killer Cell Cytotoxicity
(n = 15 CFS Patients)

|   | Age | Sex | 0 hr Ratio 125:1 0 ug/ml AMPLIGEN® | 0 hr Ratio 25:1 0 ug/ml AMPLIGEN® | 20 hr Ratio 125:1 0 ug/ml AMPLIGEN® | 20 hr Ratio 125:1 25 ug/ml AMPLIGEN® | 20 hr Ratio 125:1 % Change | 20 hr Ratio 25:1 0 ug/ml AMPLIGEN® | 20 hr Ratio 25:1 25 ug/ml AMPLIGEN® | 20 hr Ratio 25:1 % Change |
|---|---|---|---|---|---|---|---|---|---|---|
| 1 | 55 | M | 18.8 | 27.8 | 11.5 | 9.7 | −16% | 18.6 | 19.2 | 3% |
| 2 | 59 | F | 13.9 | 21.5 | 30.5 | 46.5 | 52% | 41.4 | 53.8 | 30% |
| 3 | 57 | F | 14.5 | 25 | 33.8 | 44.7 | 32% | 40.5 | 55.7 | 38% |
| 4 | 46 | F | 40.5 | 26.8 | 9.1 | 21 | 131% | 17.5 | 35.5 | 103% |
| 5 | 49 | M | 6.3 | 9.7 | 5.1 | 7.4 | 45% | 7.3 | 8.9 | 22% |
| 6 | 26 | F | 1.7 | 2 | 5.8 | 12.2 | 110% | 12.5 | 20.2 | 62% |
| 7 | 41 | F | N/A | N/A | 1.2 | 7.2 | 500% | 2.3 | 4.6 | 100% |
| 8 | 51 | M | 19.7 | 28.3 | 7.8 | 26.5 | 240% | 13.2 | 30.7 | 133% |
| 9 | 39 | F | 6.2 | 13.2 | 3.5 | 7.5 | 114% | 6.3 | 16 | 154% |
| 10 | 55 | M | N/A | N/A | 13.5 | 27 | 100% | 18.9 | 36.1 | 91% |
| 11 | 45 | F | 7.1 | 15.1 | 5.1 | 8.5 | 67% | 11.2 | 16.2 | 45% |
| 12 | 43 | M | N/A | N/A | 12 | 35.5 | 196% | 26.4 | 42.4 | 61% |
| 13 | 61 | F | 15.9 | 29.2 | 38.9 | 31.7 | −19% | 45.4 | 34.8 | −23% |
| 14 | 44 | F | 9.2 | 10.6 | 15.3 | 23.5 | 54% | 25.7 | 36.4 | 42% |
| 15 | 42 | F | N/A | N/A | 0.5 | 5.8 | 1060% | 2.9 | 10.5 | 262% |
|   | 47.53 |   | MEAN |   |   |   | 178% |   |   | 75% |
|   | 46.00 |   | MEDIAN |   |   |   | 100% |   |   | 61% |

TABLE 2

Dose Response Effect of Intraperitoneal (IP) AMPLIGEN® on Increasing Splenic NK Cell Activity and Peritoneal Macrophage

| Group | NK Activity (% lysis) YAC-1 | Macrophage Activity (% lysis/inhibition) LL target |
|---|---|---|
| Naïve | 25.9 ± 0.6 | 31.6 ± 1.4 |
| AMPLIGEN® (8 mg/kg) | 60.0 ± 1.0* | 62.2 ± 1.7* |
| AMPLIGEN® (4 mg/kg) | 59.8 ± 1.9* | 49.6 ± 1.7* |
| AMPLIGEN® (2 mg/kg) | 56.2 ± 0.7* | 46.6 ± 3.2* |
| AMPLIGEN® (1 mg/kg) | 58.0 ± 1.1* | 38.1 ± 2.0 |

In Table 2, "*" indicates that statistically significant is ($p < 0.05$) as compared with naive control.

Based on the above, it can be seen that AMPLIGEN® has a beneficial effect in increasing both Natural Killer cell activity and macrophage activity and the effect is substantial at all dosage levels tested (i.e., 1 mg/kg, 2 mg/kg, 4 mg/kg and 8 mg/kg). Substantial effects were seen even when the dosage was 1 mg/kg.

Example 5: AMPLIGEN® Enhances Cellular Immunity in Humans

Delayed-type hypersensitivity (DTH) response is an important index of cellular immunity. It is known that cellular immunity is suppressed in patients with endometriosis as well as patients with advanced HIV disease.

In this experiment, mean delayed-type hypersensitivity reactivity in seven subjects with HIV disease who received up to 40 weeks of AMPLIGEN® treatment (400 mg IV twice weekly) were measured and charted in FIG. 1. The mean number of responses to the applied antigens (mumps, *trichophyton*, and tetanus toxoid) were analyzed prior to AMPLIGEN® administration (baseline) and at 8-week intervals after initiation of AMPLIGEN® therapy. A significant correlation between time on therapy and mean reactivity was observed ($p<0.05$, ANOVA). Baseline through week 24, n=7; weeks 32 and 40, n=6. The data indicate that AMPLIGEN® can increase cellular immunity in a host suffering from cellular immunity suppression when administered. As discussed, it is known that endometriosis is correlated with suppressed cellular immunity and, suppressed cellular immunity reduces the body's ability to remove or suppress ectopic growth in the peritoneal cavity. Therefore, based on this data, it is expected that administration of tdsRNA such as AMPLIGEN® to a subject will treat or reduce the symptoms of endometriosis.

Example 6: Experimental Results for tdsRNA on Human Ectopic Growth Using Colorectal Carcinoma as a Model Additional experiments were performed to see if tdsRNA is effective in enhancing immunosurveillance. The goal of the experiment was to see if tdsRNA can reduce ectopic tumor tissue growth in the peritoneal cavity. In this case, the model for ectopic tumor tissue growth is colorectal carcinoma. The results show that tdsRNA (AMPLIGEN®) was able to increase the ratio of Effector T cells to Regulatory T cells ($T_{effector}/T_{reg}$) in the peritoneal cavity—colorectal carcinoma microenvironment.

In performing the study, colorectal carcinoma biopsy specimens were used as a model of ectopic growth. The tdsRNA used was AMPLIGEN® and this tdsRNA was administered to determine if there is an improvement in the $Teff/T_{reg}$ ratio in the tumor microenvironment. The improvement of the $T_{eff}/T_{reg}$ ratio should be secondary to the AMPLIGEN® induction of desirable chemokines while decreasing the unfavorable chemokines. In this case, CXCL 10 ($T_{eff}$-attractant) was analyzed as the desirable chemokine while CCL22 ($T_{reg}$-attractant) was analyzed as the undesirable chemokine. If tdsRNA administration was successful, it is expected that an increase in the $T_{eff}/T_{reg}$ ratio in the peritoneal cavity—colorectal carcinoma microenvironment would be observed.

Figure 2:
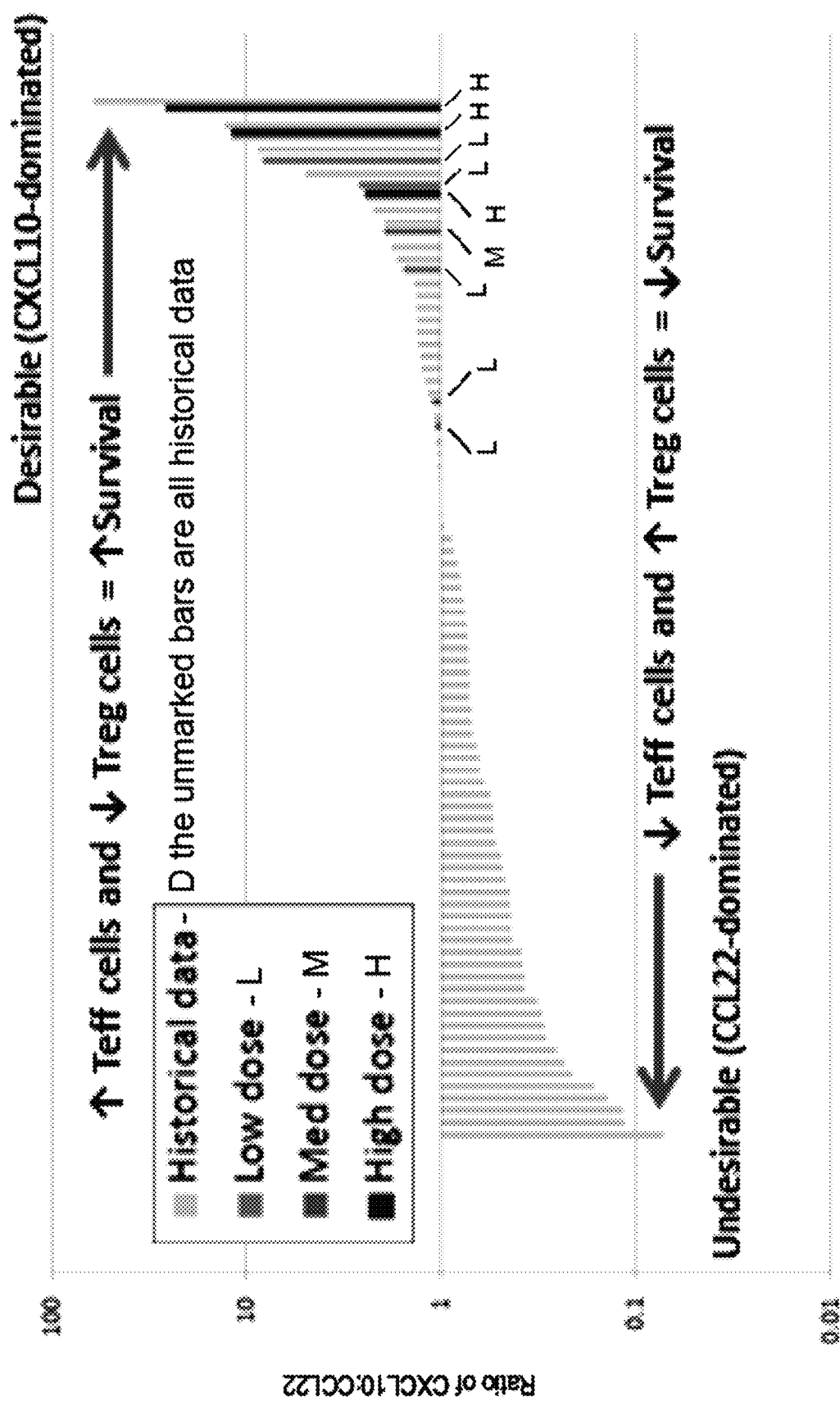
FIG. 2 depicts significantly improved the ratio of CXCL10 ("good"):CCL22 ("bad") chemokines in tumor samples vs. historical data similarly collected (p=0.0015).
Figure 3:
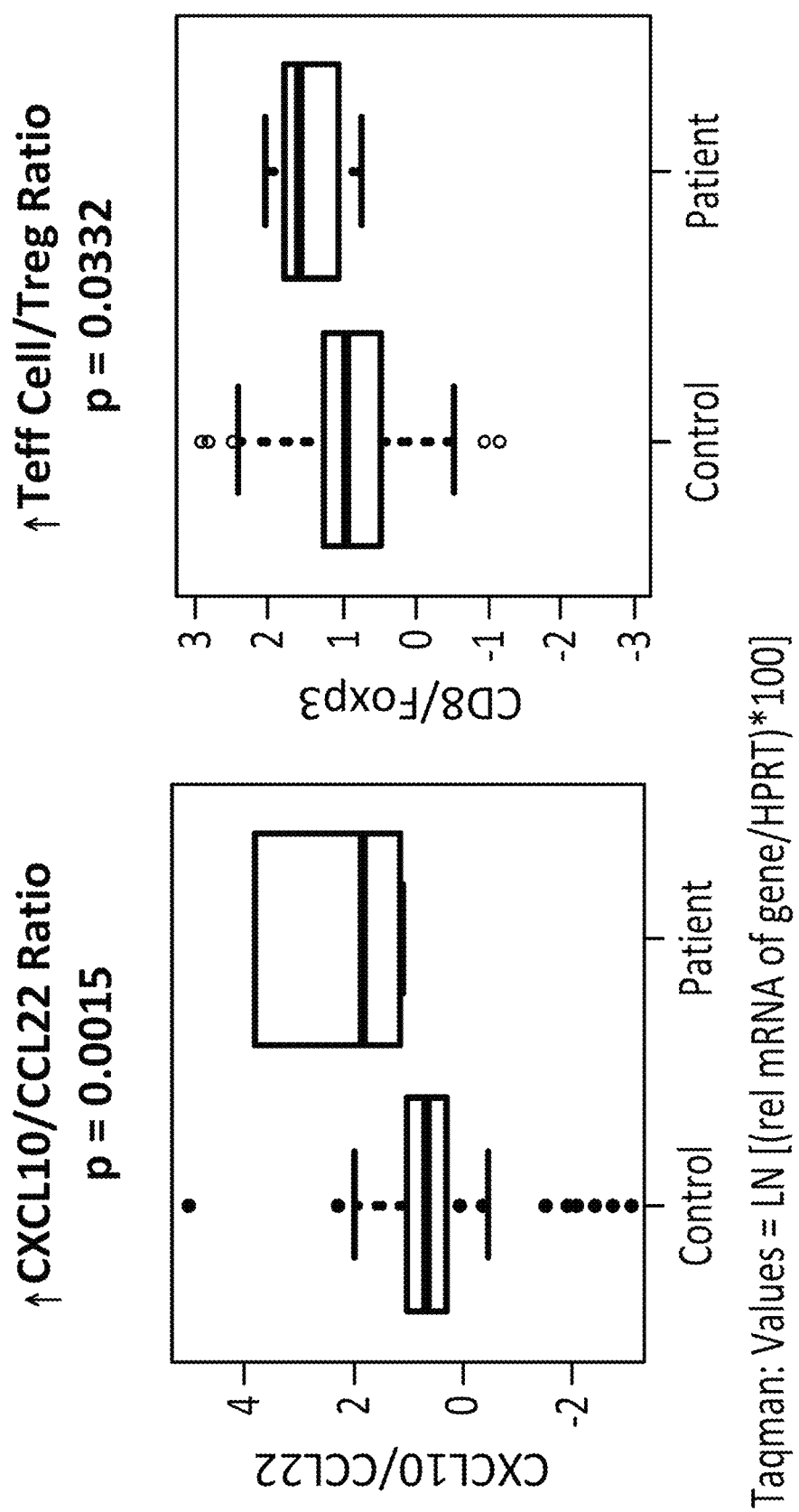
FIG. 3 depicts the ratios of chemokines and T cell markers in resected tumors following tdsRNA (AMPLIGEN®) treatment (Phase I/II Patients vs. Historical Controls).

The results of this experiment are shown in FIG. 2 and FIG. 3. These figures show that AMPLIGEN® plus rIFNa-2b and celecoxib produced an increased ratio of CXCL10 to CCL22 in the tumor microenvironment along with an increase in the ratio of $T_{eff}/T_{reg}$ markers in 9 patients with metastatic colorectal carcinoma compared to historical controls. See FIG. 2 which depicts a significantly improved ratio of CXCL10 ("good"):CCL22 ("bad") chemokines in tumor samples vs. historical data similarly collected (p=0.0015). See, for example, that the ratio is significantly improved with higher doses of tdsRNA. See, also, FIG. 3 which depicts the ratios of chemokines and T cell markers in resected tumors following AMPLIGEN® treatment (Phase I/II Patients vs. Historical Controls).

It was found that that AMPLIGEN® plus checkpoint blockade (e.g., caused by administration of a checkpoint inhibitor) synergistically increased survival in colorectal carcinoma.

Figure 4:
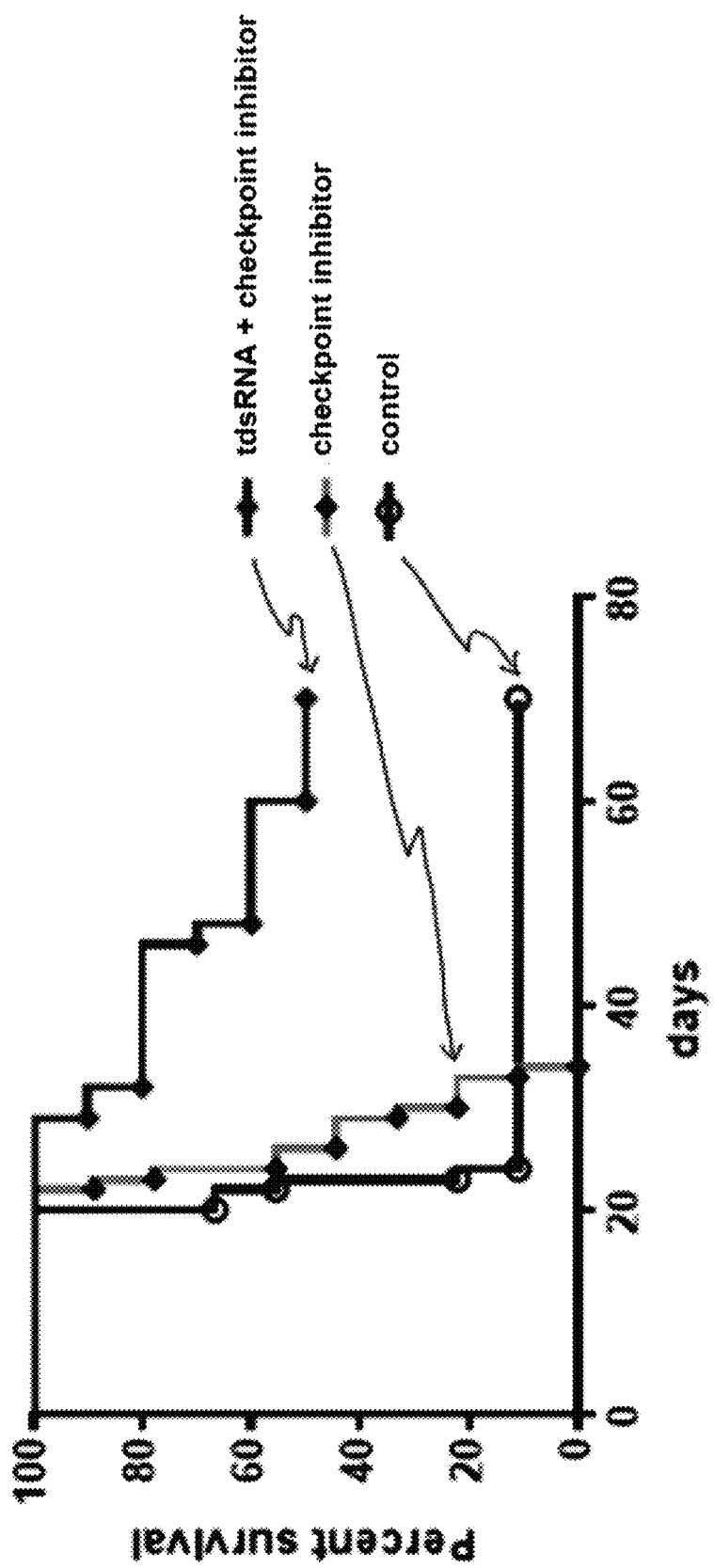
FIG. 4 is a graph showing that a combination of tdsRNA (AMPLIGEN®) plus anti-PD-1 (Rmp1-14) increases survival of greater than 250% compared to anti-PD-1 (Rmp1-14) alone.

In a separate experiment, in a mouse model of ectopic peritoneal cavity tumor using colorectal carcinoma as a model, the combination of tdsRNA plus a checkpoint inhibitor showed a median survival increase of greater than 250% compared to checkpoint inhibitor alone. See, FIG. 4. In FIG. 4, the tdsRNA is AMPLIGEN® and the checkpoint inhibitor is Rmp1-14 (anti-PD-1).

The experiments clearly showed that AMPLIGEN® (rintatolimod) has an ability to convert "cold" ectopic tumors into "hot" ectopic tumors in the peritoneal cavity making such ectopic tissues much more likely to respond to cellular immunity with the relief of symptoms As further support, positive results were also observed when tdsRNA was applied to ectopic peritoneal cavity tumor using mouse bladder carcinoma as a model. In this experiment, AMPLIGEN® alone significantly inhibited the growth of human bladder tumor xenografts in nude mice and appeared to work, at least in part, by an immune-enhancing mechanism.

Example 7: Mouse Combinatorial Immunotherapy of AMPLIGEN® (Rintatolimod) Poly I:Poly $C_{12}U$ and Blockade of Programmed Death-Ligand 1 Against Established Melanoma Tumors in a Mouse Model This series of experiments shows that tdsRNA (e.g., AMPLIGEN®) induced synergy for suppressing ectopic peritoneal cavity tumor when it is administered with checkpoint blockade. Specifically, the data indicate that:

(1) tdsRNA was synergistic with anti-PD-L1, yielding an increased anti-tumor response in a B16 mouse melanoma model.

(2) The anti-tumor effect was significantly greater for the tdsRNA 250 µg+anti-PD-L1 cohort compared to anti-PD-L1 cohort alone (p=0.023).

(3) addition of tdsRNA to anti-PD-L1 increased the objective response rate of 300%, from 10% with anti-PD-L1 alone to 30% with the combination.

The studies were conducted as follows:

For the series of experiments in this Example, the tdsRNA used was AMPLIGEN®. tdsRNA and anti-PD-L1 antibodies were tested for their ability to suppress peritoneal cavity ectopic growth against established subcutaneous B16 melanoma tumors in C57BL/6 mice. Briefly, mice (10 animals per group) were inoculated with 0.4×10E6 (i.e., 400,000) B16-F10 tumor cells in their shaved rear flanks causing ectopic growth. Seven days later, mice were randomized to six treatment groups as follows: (Group 1) No treatment (negative controls); (Group 2) tdsRNA alone 100 µg/dose 4×; (Group 3) tdsRNA alone 250 µg/dose 4×; (Group 4) Anti-PD-L1 mAb alone; (Group 5) tdsRNA 100 µg/dose 4× plus anti-PD-L1 mAb; (Group 6) tdsRNA 250 µg/dose 4× plus anti-PD-L1 mAb. mAb refers to monoclonal antibody.

tdsRNA was injected IV at 100 or 250 µg/dose 4 times, 5 days apart. Anti-PD-L1 mAb was administered IP on Days 1 and 3 after each tdsRNA dose at 200 µg/dose. Tumors were measured 3 times per week using calipers, measuring 2 opposing diameters. Mice exhibiting ulcerated tumors or tumors greater than 2 cm in diameter were euthanized starting on day 14. This confounded the analysis of tumor sizes after day 12. Results were presented as tumor sizes for individual mice throughout time of therapy up to Day 30.

The data shows that tdsRNA 250 µg+anti-PD-L1 cohort had more than one significant tumor regression as seen in the data and Tables presented below:

TABLE 6

Only the tdsRNA 250 µg + anti-PD-L1 Cohort had More than One Significant Tumor Regression at Day 30*

| Group (n = 10) | Number of Complete Responses (CR) | Number of Partial Responses (PRs) | % Tumor Reduction in PRs | Total # Tumor Responses CR + PR |
|---|---|---|---|---|
| No Treatment Control | 0 | 0 | — | 0 |
| 100 µg tdsRNA | 0 | 0 | — | 0 |
| 250 µg tdsRNA | 0 | 0 | — | 0 |
| Anti-PD-L1 | 10% | 0 | — | 10% |
| 100 µg tdsRNA + Anti-PD-L1 | 10% | 0 | — | 10% |
| 250 µg tdsRNA + Anti-PD-L1 | 10% | 20% | 70% and 86% | 30% |

TABLE 6-continued

Only the tdsRNA 250 µg + anti-PD-L1 Cohort had
More than One Significant Tumor Regression at Day 30*

| Group (n = 10) | Number of Complete Responses (CR) | Number of Partial Responses (PRs) | % Tumor Reduction in PRs | Total # Tumor Responses CR + PR |
|---|---|---|---|---|

Tumor assessments were performed per RECIST v1.1 criteria

In addition, synergistic effects by day 9 were observed as follows:

TABLE 7

Changes in Tumor Size at Day 9: Synergistic
Effect of Combining tdsRNA + Anti-PD-L1 (p = 0.023+)
Changes in Tumor Size from Day $0^\Delta$ to Day 9;
Tumor Size Changes measured in mm$^2$

| Mouse # | Anti-PD-L1 Only | tdsRNA 250 µg + Anti PD-L1 |
|---|---|---|
| 1 | 1.10 (CR) | −15.66* |
| 2 | −12.19* | −2.27* (PR) |
| 3 | 61.99 | 22.88 |
| 4 | −3.48* | 25.35 |
| 5 | 78.44 | −11.28* (PR) |
| 6 | 55.94 | −13.51* (CR) |
| 7 | 4.65 | −18.33* |
| 8 | 23.15 | −10.48* |
| 9 | 49.56 | −14.20* |
| 10 | 0.09 | 9.77 |
| Totals | 259.3 | −27.7* |

*= Negative values (i.e., tumors decreased in size)
+ ANOVA
$^\Delta$First tumor size measurement and first dose of tdsRNA occurred on Day 0

Synergism was also seen in a decrease in tumor size at follows:

TABLE 8

A Significantly Greater Number of Tumors in the
tdsRNA 250 µg + Anti-PD-L1 Cohort Decreased in Size
Comparison of the Number of Tumors Which
Decreased in Size at Day 9 Compared to Day $0^\Delta$

| Mouse Cohort | Number of Tumors Increased in Size | Number of Tumors Decreased in Size | p-value |
|---|---|---|---|
| No Treatment Control (n = 10) | 10 | 0 | 0.0025* |
| Anti-PD-L1 Only (n = 10) | 8 | 2 | 0.0025* |
| 250 µg tdsRNA + Anti-PD-L1 (n = 10) | 3 | 7 | 0.0025* |

*Fisher's Exact Test (2-sided)
$^\Delta$First tumor size measurement and first dose of tdsRNA occurred on Day 0

Increase in Tumor Size at Day 12 was 5.2 Times Greater in the Anti-PD-L1 Cohort Compared to the tdsRNA 250 µg+Anti-PD-L1 Cohort (p=0.023±)

TABLE 9

Changes in Tumor Size from Day $0^\Delta$ to Day 12

| Mouse # | Tumor Size Change (mm$^2$) Anti-PD-L1 Only | tdsRNA 250 µg + Anti PD-L1 |
|---|---|---|
| 1 | −5.16* (CR) | −7.45* |
| 2 | −10.13* | −8.33* (PR) |
| 3 | 153.54 | 46.78 |
| 4 | 14.85 | 48.65 |
| 5 | 167.07 | −11.00* (PR) |
| 6 | 153.78 | −13.74* (CR) |
| 7 | 31.06 | 7.28 |
| 8 | 33.35 | −0.98* |
| 9 | 79.55 | −5.34* |
| 10 | −1.78* | 62.81 |
| Mean Tumor Size | 61.6 | 11.9 |

*= Negative values (i.e., tumors decreased in size)
+ ANOVA
$^\Delta$First tumor size measurement and first dose of tdsRNA occurred on Day 0

In conclusion, tdsRNA was synergistic with anti-PD-L1 yielding an increased suppression of ectopic growth in the peritoneal cavity in this model. At both Days 9 and 12 the ectopic tumor suppression effect was significantly greater for the tdsRNA 250 µg+anti-PD-L1 cohort compared to anti-PD-L1 cohort alone (p=0.023). Tumor suppression and reductions were seen at Days 9 and 12 in the tdsRNA 250 µg+anti-PD-L1 cohort translated into 1 CR and 2 PRs by Day 30. Thus, compared to the one CR seen in the anti-PD-L1 alone cohort, or a 10% overall response rate, the tdsRNA 250 µg+anti-PD-L1 cohort had a 30% overall response rate at Day 30.

Example 8: Experimental Results for tdsRNA on Ectopic Growth Using Mouse Renal Carcinoma as a Model Positive results were seen with renal carcinomas (also referred to in this disclosure as renal cell cancer, renal cell carcinoma, kidney cancer).

Renal Cell Carcinoma

Anti-tumor activity of AMPLIGEN® on human renal cell carcinoma xenografts (786-O) in nude mice. Mismatched dsRNA caused statistically significant tumor growth inhibition (p<0.001) and survival (p<0.002) (Hubbell, 1990).

Figure 5:
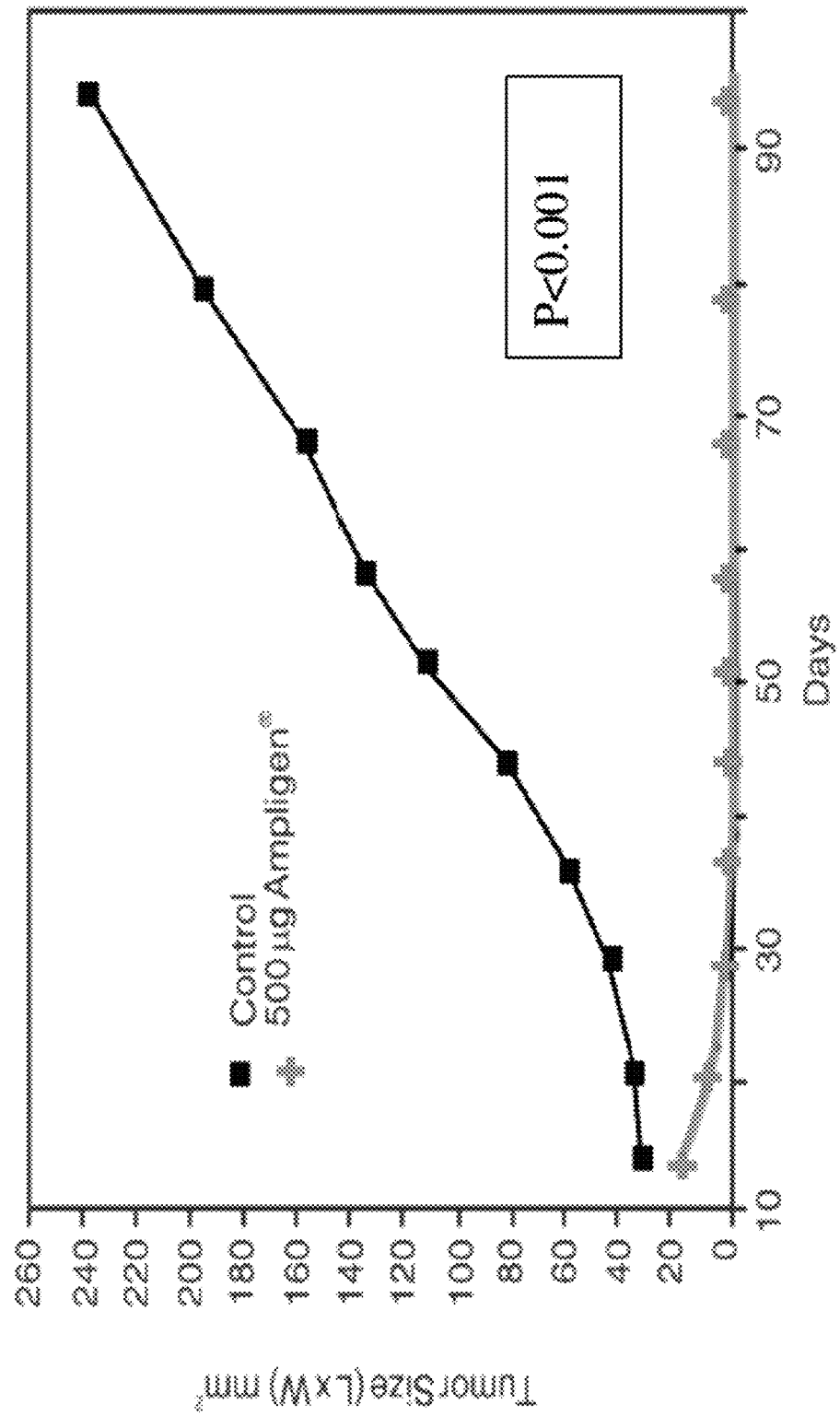
FIG. 5 depicts the ability of tdsRNA (AMPLIGEN®) to suppress the growth of ectopic tissue (786-0 xenografts).
Figure 6:
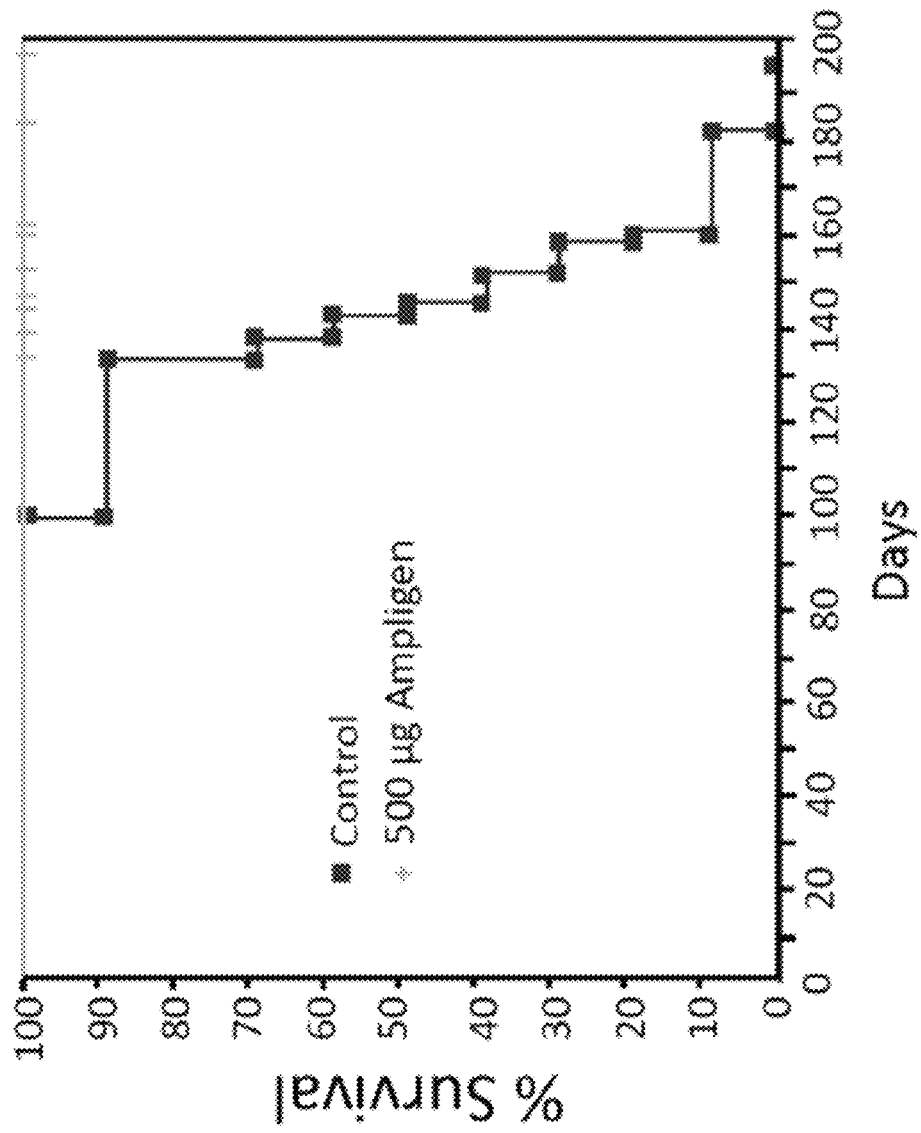
FIG. 6 depicts the survival of tumor-bearing nude mice 786-0 xenografts treated with tdsRNA (AMPLIGEN®).

FIG. 5 and FIG. 6 illustrate results of rintatolimod (AMPLIGEN®) given as a monotherapy, where AMPLIGEN® demonstrated an ability to increase anti ectopic tumor immune mechanisms and survival in a mouse renal cell carcinoma xenograft (786-O) model. Results indicate that AMPLIGEN® has direct anti-tumor effects and its augmentation of innate immune responses (NK cells) could have a key role in suppressing ectopic growth and tumor regression. As shown in FIG. 5 and FIG. 6, AMPLIGEN® was effective at both inhibiting ectopic growth (tumor regression was observed in each mouse) and increasing survival, where 90% of mice given AMPLIGEN® were free of residual ectopic tumor growth while 100% of the control group had died.

Example 9: Experimental Results for tdsRNA on Human Ectopic Growth Using Pancreatic Cancer as a Model Pancreatic cancer is associated with an overall five-year survival of 5% and thus contributes significantly to cancer-related mortality. A recent paper predicted that pancreatic cancer will be the second leading cause of cancer-related deaths before 2030. Currently, surgery is the only potentially curative option, but only around 15% of patients are eligible at initial diagnosis since most pancreatic cancers are detected in an advanced stage of the disease. Around 20% of patients are diagnosed with locally advanced pancreatic cancer, and about 30-65% present with metastatic disease. It is clear that new treatment options are desperately needed for this devastating malignancy.

The current standard of care (SOC) for locally advanced and metastatic pancreatic carcinoma is FOLFIRINOX, a four-drug cocktail with significant toxicity. Approval of FOLFIRINOX was based on the Phase 2/3 ACCORD study published in 2011 (Von Hoff et al., 2011). In this study, FOLFIRINOX was compared to Gemcitabine, which was the SOC at that time.

The result of the ACCORD study is that overall survival (OS) increased from 6.8 months with Gemcitabine to 11.1 months with FOLFIRINOX (p<0.001). However, the Complete Response Rate (CR) was only 0.6%. Moreover, overall mean survival with second-line therapy following progression on the FOLFIRINOX was only 4.05 months. The data clearly shows that the new treatment options are desperately needed for this devastating malignancy.

One of these novel therapeutic options is immunotherapy, which has shown to be a promising treatment strategy. Essential in this therapeutic strategy is to boost the patient's immune system, by reversing the tumor-antigen-specific T-cell tolerance induced by their tumor.

One goal in immunotherapy is the reprograming of the microenvironment of the ectopic growth—which is the tumor microenvironment (TME)—to convert "cold" tumors into "hot" tumors that will be responsive to checkpoint blockade and be responsive to suppression or elimination by cellular immunity. The goal is to unleash the cellular immune response to attack and destroy cancer cells and increase survival by increasing intratumoral $T_{\mathit{eff}}$ cells while decreasing intratumoral $T_{\mathit{reg}}$ cells.

Surprisingly, tdsRNA in the form of AMPLIGEN® is capable of promoting the selective attraction of CTLs ($T_{\mathit{eff}}$) with a concomitant reduction in $T_{\mathit{reg}}$ attraction in the tumor microenvironment based on our observations.

An ability to increase $T_{\mathit{eff}}$ (CD8+ T cells) and reducing $T_{\mathit{reg}}$ cells in the tumor microenvironment has significant advantages. In Pancreatic Cancer, the ratio of the panel of tumor-infiltrating CD8+T effector cells to the level of CD4+ regulatory T cells in the tumor microenvironment is an independent prognosticator of overall survival. An increased ratio (e.g., (CD8+ effector T cells)/(CD4+ regulatory T cells)) is a good prognostic indicator.

In pancreatic cancer, $T_{\mathit{reg}}$ infiltration into the tumor microenvironment is a bad prognostic indicator for survival. Hiraoka et al. divided pancreatic cancer patients into two cohorts based on values of the $T_{\mathit{reg}}$ cells being higher or lower than the median value in the tumor microenvironment, the low $T_{\mathit{reg}}$ group showed significantly better survival than the high $T_{\mathit{reg}}$ group (Hiraoka, et al., 2006).

Our discovery that AMPLIGEN® can increase the $T_{\mathit{eff}}$ cell to $T_{\mathit{reg}}$ cell ratio ($T_{\mathit{eff}}/T_{\mathit{reg}}$) thereby converting a "cold" pancreatic tumor microenvironment into a "hot" pancreatic tumor microenvironment is highly relevant for improving the likelihood of an anti-tumor response to checkpoint blockade.

Experimental Results

AMPLIGEN® was tested in mice against pancreatic tumors in conjunction with an anti-PD-L1. The combination was shown to synergistically increase survival as well as time to tumor progression (p=0.029 and 0.0418, respectively). The data is shown below.

TABLE 4

Initial Results from Mouse Model of Pancreatic Cancer Using AMPLIGEN® Plus Checkpoint Blockade

| Cohorts (n = 8 each) | Time to Progression Median-Days |
|---|---|
| 1) Control | 33 |
| 2) AMPLIGEN® | 33 0* |
| 3) Anti-PD-L1 | 33 0* |
| 4) AMPLIGEN® + Anti-PD-L1 | 73 40* |

*Increased Survival Over Control

Figure 7:
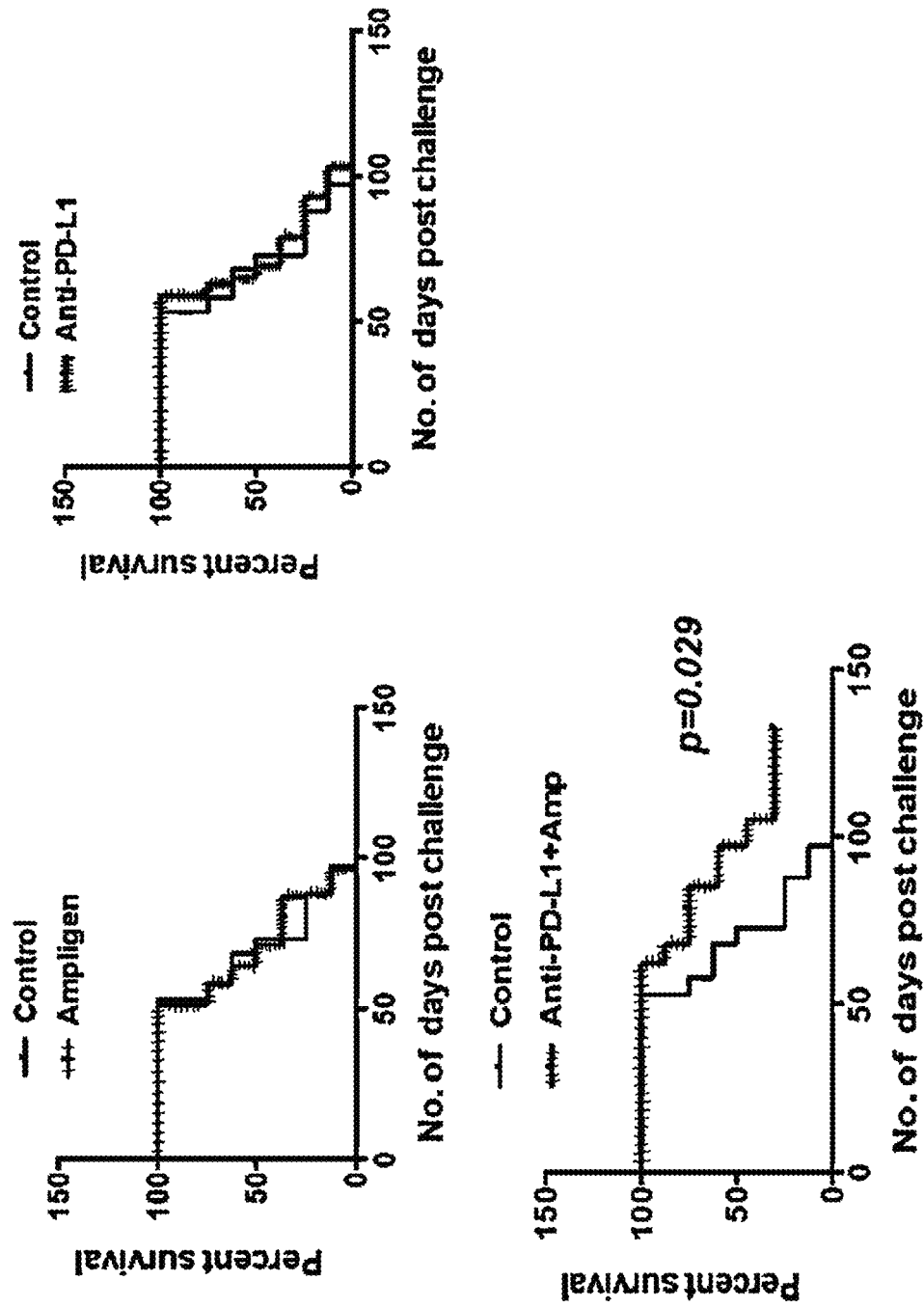
FIG. 7 depicts the synergism between tdsRNA (AMPLIGEN®) and checkpoint blockade in suppressing ectopic growth and tumor progression.
Figure 7:
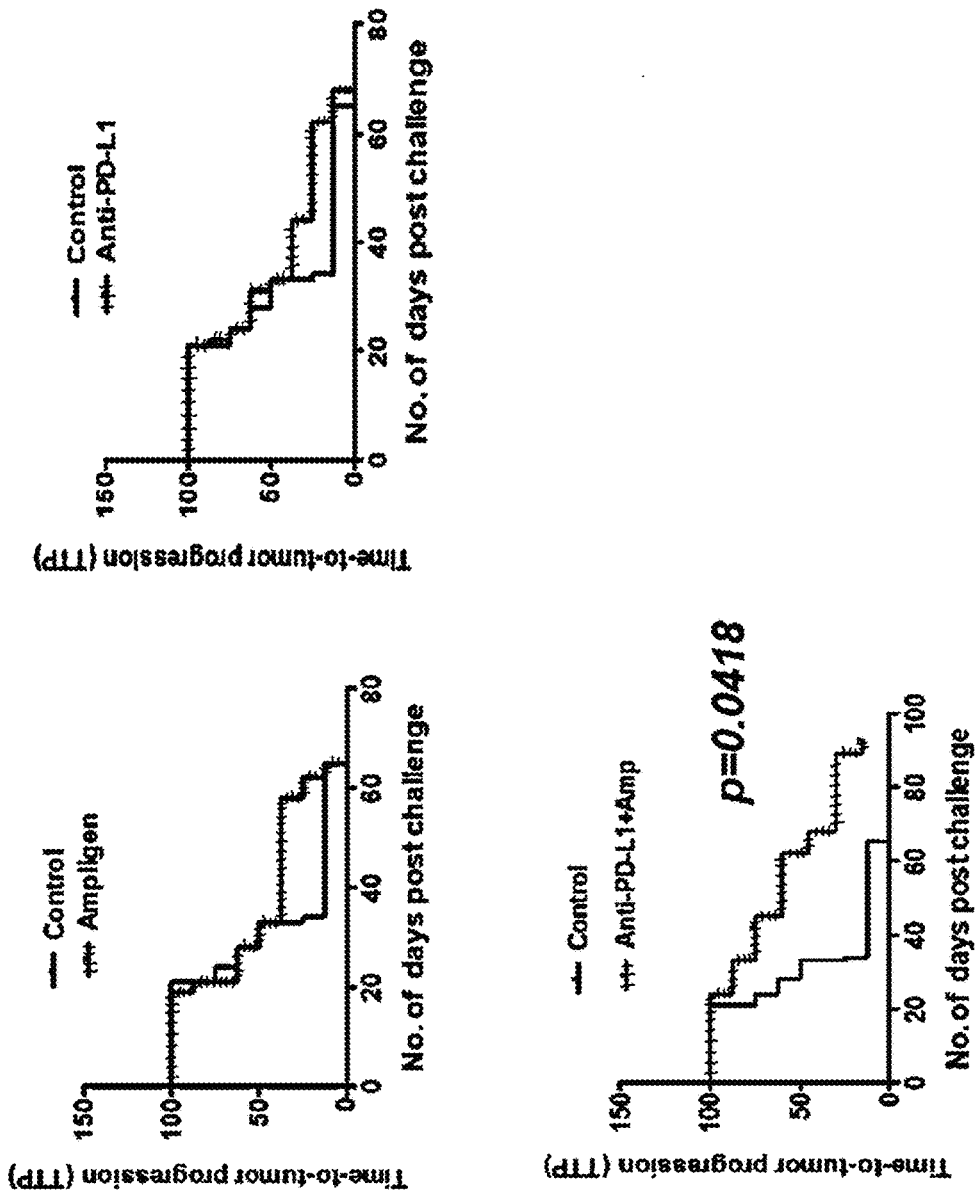

This data is also plotted in FIG. 7. From the data, it is clear that time to progression and survival are both increased. tdsRNA and checkpoint blockade (anti-PD-L1) are found to be synergistic for increasing both overall survival and time-to-tumor progression. See, FIG. 7.

This disclosure also supports the use of tdsRNA in combination with checkpoint blockade to improve the ability to treat endometriosis. More specifically, the data support that tdsRNA and the checkpoint blockade can perform synergistically. That is, the effect of a combination of tdsRNA (effect of tdsRNA+checkpoint blockade) is greater than that of the sum of each individual component alone (i.e., effects of tdsRNA alone+effect of checkpoint blockade alone.

Example 10: Combinatorial Immunotherapy of AMPLIGEN® (Rintatolimod) Poly I:Poly $C_{12}U$ and Blockade of Programmed Death-Ligand 1 Against Established Melanoma Tumors in a Mouse Model Positive results were also shown in a mouse melanoma model. Experiments were to show that the combination of rIL-2 and AMPLIGEN® can potentiate host-mediated anti-tumor effects, yielding increased survival in a melanoma xenograft model without toxicity.

AMPLIGEN® together with anti-PD-L1 antibodies were tested for anti-tumor activity against established subcutaneous B16 melanoma tumors in C57BL/6 mice. Mice (10 animals per group) were inoculated with 0.4×10E6 B16-F10 tumor cells in their shaved rear flanks. Seven days later (when tumors reached 0.3 to 0.5 cm in their largest diameter), mice were randomized for tumor sizes, and individually tagged and were allocated to the following six treatment groups: (1) No treatment (negative controls); (2) AMPLIGEN® alone 100 µg/dose 4×; (3) AMPLIGEN® alone 250 µg/dose 4×; (4) Anti-PD-L1 mAb alone; (5) AMPLIGEN® 100 µg/dose 4× plus anti-PD-L1 mAb; and (6) AMPLIGEN® 250 µg/dose 4× plus anti-PD-L1 mAb.

AMPLIGEN® was injected intravenously at 100 or 250 micrograms/dose and was repeated 4 times, 5 days apart. Anti-PD-L1 mAb (clone 10F.9G2, BioXCell) was administered intraperitoneally on Days 1 and 3 after each AMPLIGEN® injection at a 200 microgram/dose. Tumors were measured 3 times per week using a set of calipers, taking measurement of 2 opposing diameters and were recorded as tumor areas. Mice exhibiting ulcerated tumors or tumors larger than 2 cm diameter (any direction) were euthanized following IACUC policies.

Results were presented as tumor sizes for individual mice throughout time of therapy, average tumor size in each group and survival up to Day 30 (time to euthanasia).
Results:
Tumor Responses at Day 30
One complete tumor regression was seen by Day 30 in each of the three (3) cohorts that received the anti-PD-L1 mAb. The only cohort that had more than one significant tumor regression was the AMPLIGEN® 250 µg+anti-PD-L1 group. As shown in the next Table below, the AMPLIGEN® 250 µg+anti-PD-L1 group had two mice with partial responses (PRs) of 70 and 86% reductions in the tumor size (per RECIST v1.1 criteria) in addition to the complete response (CR).
Summary of Tumor Responses:
The experimental data shows that AMPLIGEN® was synergistic with anti-PD-L1, yielding an increased anti-tumor response in a B16 mouse melanoma model
The decrease in tumor size was significant for the AMPLIGEN® 250 µg+anti-PD-L1 cohort compared to anti-PD-L1 cohort alone (p=0.023).
Addition of AMPLIGEN® to anti-PD-L1 increased the objective response rate 3-fold, from 10% with anti-PD-L1 alone to 30% with the combination.

TABLE 5

Tumor Responses*

| Group (n = 10) | Number of Complete Responses (CR) | Number of Partial Responses (PR) | % Tumor Reduction in PRs | Total # Tumor Responses CR + PR |
|---|---|---|---|---|
| No Treatment Control | 0 | 0 | — | 0 |
| 100 µg AMPLIGEN® | 0 | 0 | — | 0 |
| 250 µg AMPLIGEN® | 0 | 0 | — | 0 |
| Anti-PD-L1 | 1 | 0 | — | 1 |
| 100 µg AMPLIGEN® + Anti-PD-L1 | 1 | 0 | — | 1 |
| 250 µg AMPLIGEN® + Anti-PD-L1 | 1 | 2 | 70% and 86% | 3 |

*Tumor assessments were performed per RECIST v1.1. criteria.

Example 11: Summary of Previous Examples Showing tdsRNA and Checkpoint Inhibitor Synergistically Increased Survival The data disclosed herein show that tdsRNA (AMPLIGEN®) has a beneficial effect on enhancing immunosurveillance to reduce ectopic growth from a variety of models. Specifically, tdsRNA can reverse the symptoms of endometriosis such as (1) decrease in macrophage activity; (2) decrease in NK cell activity; and (3) decrease in T effector cell/T regulatory cell ratio.

It is also shown that a combination of tdsRNA with a checkpoint inhibitor can suppress ectopic tissue growth leading to an increase in median survival.

In a mouse model of colorectal carcinoma, the combination of tdsRNA plus anti-PD-I showed a median survival increase of greater than 250% compared to anti-PD-I alone. Results in a melanoma model points to a similar conclusion. tdsRNA and a checkpoint inhibitor were synergistic yielding an increased anti-tumor response in a B16 mouse melanoma model. The decrease in tumor size was significant for tdsRNA (AMPLIGEN®) 250 µg+anti-PD-LI cohort compared to anti-PD-LI cohort alone (p=0.023). Addition of tdsRNA to anti-PD-LI increased the objective response rate 300%, from 10% with anti-PD-LI alone to 30% with the combination. In addition, in a transgenic mouse model, administering tdsRNA with a checkpoint inhibitor to a pancreatic cancer model shows a synergistic increase in median survival.

Example 12: Clinical Site #1: Treatment of Endometriosis in Trial Participants

Based on the research and data above, experiments were performed to see if tdsRNA (e.g., AMPLIGEN®) may be effective in treating endometriosis. Endometriosis is characterized by ectopic growth of tissue outside their normal area—much like the beginning stages of malignancy. It is hypothesized that tdsRNA may change the microenvironment in endometriosis tissue growth to increase, for example the ratio of $T_{eff}/T_{reg}$ and thereby activate $T_{eff}$ to cause regression of ectopic endometriosis tissue.

To experimentally test the hypothesis, 23 female trial participants were tested. Of the 23 participants, 6 were previously diagnosed with endometriosis while the remainder shows symptoms consistent with endometriosis (referred to herein in this Example section as endometriosis symptoms). These symptoms include: dyspareunia; dysmenorrhea; chronic pelvic pain; dyspareunia; dysuria; mittelschmerz; interstitial cystitis; pelvic inflammatory disease; and bodily movement pain present during exercise, standing and walking. 32% reported a history of symptoms of pelvic inflammatory disease and/or interstitial cystitis. The latter being the most common among this group of patients.

The tools used to assess endometriosis-related pain is the visual analog scale (VAS) and general quality of life scales. See, Bourdel, N., et al., Systematic review of endometriosis pain assessment: how to choose a scale? Hum Reprod Update, 2015. 21(1): p. 136-52.

AMPLIGEN® (rintatolimod) was given i.v. 200 mg twice weekly for 2 weeks, then 400 mg twice weekly for the duration of the study. After about 24 to 40 weeks of treatment, 18 of the 23 participants had a significant reduction in endometriosis symptoms and significant improvements in overall mood.

Example 13: Clinical Site #2—Treatment of Endometriosis in Trial Participants

This study tested 8 female trial participants were tested. These trial participants were previously diagnosed with endometriosis (referred to herein in the Example section as endometriosis symptoms). These symptoms include: dyspareunia; dysmenorrhea; chronic pelvic pain; dyspareunia; dysuria; mittelschmerz; interstitial cystitis; pelvic inflammatory disease; and bodily movement pain present during exercise, standing and walking. Furthermore, each participant reported a history of further symptoms of interstitial cystitis and/or pelvic inflammatory disease.

The tools used to assess endometriosis-related pain are the review of symptoms questionnaire and medical records history at the initial visit.

AMPLIGEN® (rintatolimod) was given i.v. 200 mg twice weekly for 2 weeks, then 400 mg twice weekly for the duration of the study.

After about 24 to 48 weeks of treatment, 6 of the 8 participants had a significant reduction in endometriosis symptoms.

We claim:

1. A method for treating endometriosis or ameliorating a symptom of endometriosis in a subject comprising
    administering to the subject a therapeutically effective amount of a pharmaceutical composition comprising as an active ingredient a therapeutic double stranded RNA (tdsRNA);
wherein the tdsRNA is selected from the group consisting of
    $rI_n \cdot r(C_xU)_n$; and
    rugged dsRNA;
    wherein x is one or more selected from the group consisting of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 4-29, 11-14, and 30-35, wherein n is from 40-40,000.

2. The method of claim 1, wherein the symptom of endometriosis is at least one selected from the group consisting of dyspareunia;
    dysmenorrhea;
    chronic pelvic pain;
    dysuria;
    mittelschmerz;
    interstitial cystitis;
    pelvic inflammatory disease; and
    bodily movement pain present during exercise, standing and walking.

3. The method of claim 1, wherein the endometriosis is a reoccurring endometriosis.

4. The method of claim 1, wherein administering is at least one form of administering selected from the group consisting of:
    administering intravenously;
    administering intraperitoneally;
    administering intranasally;
    administering intradermally;
    administering subcutaneously;
    administering intramuscularly;
    administering intracranially;
    administering intravesically;
    administering orally; and
    administering topically.

5. The method of claim 1, wherein the subject is a human female.

6. The method of claim 1, wherein the tdsRNA contains a minimum of 90 weight percent of dsRNA larger than 40 basepairs.

7. The method of claim 1, wherein the tdsRNA contains a minimum of 90 weight percent of dsRNA smaller than 10,000 basepairs.

8. The method of claim 1, wherein the rugged dsRNA has
    a single strand comprised of $r(C_{4-29}U)$, $r(C_{11-14}U)_n$, or $r(C_{12}U)_n$ and
    an opposite strand comprised of r(I);
wherein the two strands do not base pair the position of the uracil base and
wherein said strands are partially hybridized.

9. The method of claim 8, wherein the rugged dsRNA has at least one selected from the group consisting of:
    the rugged dsRNA has a molecular weight of about 250 kDa to 500 kDa;
    each strand of the rugged dsRNA is from about 400 to 800 basepairs in length; and
    the tdsRNA has about 30 to 100 helical turns of duplexed RNA.

10. The method of claim 1, wherein the tdsRNA has about 4 to about 4000 helical turns of duplexed RNA strands.

11. The method of claim 1, wherein the tdsRNA has a molecular weight from about 25 kDa to about 2500 kDa.

12. The method of claim 1, wherein the tdsRNA comprises
    $rI_n \cdot r(C_{11-14}U)_n$ and
    rugged dsRNA.

13. The method of claim 1, further comprising a step of administering an interferon to the subject;
    wherein the step of administering the tdsRNA and the step of administering the interferon are performed in any order.

14. The method of claim 13, wherein the interferon is selected from the group consisting of:
    recombinant or natural interferon,
    Alferon,
    alpha-interferon species,
    recombinant or natural interferon alpha,
    recombinant or natural interferon alpha 2a,
    recombinant or natural interferon beta,
    recombinant or natural interferon beta 1b,
    recombinant interferon gamma, and
    natural interferon gamma.

15. The method of claim 13, wherein the interferon is a mixture of at least seven species of alpha-interferon produced by human white blood cells, wherein the seven species are:
    interferon alpha 2;
    interferon alpha 4;
    interferon alpha 7;
    interferon alpha 8;
    interferon alpha 10;
    interferon alpha 16; and
    interferon alpha 17.

16. A composition for treating endometriosis or ameliorating a symptom of endometriosis in a subject comprising
    tdsRNA selected from the group consisting of
    $rI_n \cdot r(C_xU)_n$ and
    rugged dsRNA;
wherein x is one or more selected from the group consisting of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 4-29, 11-14, and 30-35 wherein n is from 40-40,000.

17. The composition of claim 16, further comprising an interferon selected from the group consisting of:
    recombinant or natural interferon,
    Alferon,
    alpha-interferon species,
    recombinant or natural interferon alpha,
    recombinant or natural interferon alpha 2a,
    recombinant or natural interferon beta,
    recombinant or natural interferon beta 1b,
    recombinant interferon gamma, and
    natural interferon gamma.

18. The composition of claim 16, wherein the tdsRNA comprises
    $rI_n \cdot r(C_{11-14}U)_n$ and
    rugged dsRNA.

19. A method for treating endometriosis or ameliorating a symptom of endometriosis in a subject comprising
    administering to the subject a therapeutically effective amount of a pharmaceutical composition comprising a therapeutic double stranded RNA (tdsRNA) that is $rI_n \cdot r(C_xU)_n$;
wherein the pharmaceutical composition does not contain rugged dsRNA;

wherein x is one or more selected from the group consisting of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 4-29, 11-14, and 30-35;
wherein n is from 40 to 40,000;
wherein the tdsRNA contains a minimum of 90 wt % of dsRNA larger than 40 basepairs; and
wherein the tdsRNA contains a minimum of 90 wt % of dsRNA smaller than 10,000 basepairs.

* * * * *